US012685762B2

(12) United States Patent
Okabe et al.

(10) Patent No.: US 12,685,762 B2
(45) Date of Patent: Jul. 21, 2026

(54) AQUEOUS PHARMACEUTICAL COMPOSITION CONTAINING FUSION PROTEIN OF SERUM ALBUMIN AND GROWTH HORMONE

(71) Applicant: JCR Pharmaceuticals Co., Ltd., Ashiya (JP)

(72) Inventors: Shinji Okabe, Kobe (JP); Yuka Yamaguchi, Kobe (JP); Hidehito Yasukawa, Kobe (JP)

(73) Assignee: JCR Pharmaceuticals Co., Ltd., Ashiya (JP)

( * ) Notice: Subject to any disclaimer, the term of this patent is extended or adjusted under 35 U.S.C. 154(b) by 1044 days.

(21) Appl. No.: 17/772,908

(22) PCT Filed: Oct. 29, 2020

(86) PCT No.: PCT/JP2020/040560

§ 371 (c)(1),
(2) Date: Apr. 28, 2022

(87) PCT Pub. No.: WO2021/085518

PCT Pub. Date: May 6, 2021

(65) Prior Publication Data

US 2022/0378882 A1     Dec. 1, 2022

(30) Foreign Application Priority Data

Oct. 30, 2019    (JP) ................................. 2019-197978

(51) Int. Cl.

| | |
|---|---|
| *A61K 38/27* | (2006.01) |
| *A61K 9/08* | (2006.01) |
| *A61K 38/38* | (2006.01) |
| *A61K 47/04* | (2006.01) |
| *A61K 47/10* | (2017.01) |
| *A61K 47/26* | (2006.01) |
| *A61K 47/64* | (2017.01) |

(52) U.S. Cl.
CPC .............. *A61K 38/385* (2013.01); *A61K 9/08* (2013.01); *A61K 38/27* (2013.01); *A61K 47/26* (2013.01)

(58) Field of Classification Search
CPC ...... A61K 38/385; A61K 31/05; A61K 38/27; A61K 9/0019; A61K 47/10; A61K 47/643; C07K 2319/00; C07K 2319/31; C07K 14/61; C07K 14/765; A61P 5/06
See application file for complete search history.

(56) References Cited

U.S. PATENT DOCUMENTS

| | | | | |
|---|---|---|---|---|
| 6,150,331 A | * | 11/2000 | Tatsumi ................. | A61K 38/27 |
| | | | | 530/397 |
| 10,654,912 B2 | * | 5/2020 | Takahashi ............ | C07K 14/765 |
| 2003/0104578 A1 | | 6/2003 | Ballance | |
| 2006/0165733 A1 | * | 7/2006 | Betz ........................ | A61P 21/00 |
| | | | | 514/11.4 |
| 2010/0261650 A1 | * | 10/2010 | Ballance ................ | A61P 43/00 |
| | | | | 435/254.2 |
| 2016/0015789 A1 | | 1/2016 | Bock et al. | |
| 2018/0244754 A1 | | 8/2018 | Takahaski et al. | |
| 2019/0010205 A1 | | 1/2019 | Takahashi et al. | |
| 2019/0022183 A1 | | 1/2019 | Lim et al. | |
| 2019/0078129 A1 | | 3/2019 | Kakimoto et al. | |
| 2021/0061918 A1 | | 3/2021 | Yasukawa et al. | |

FOREIGN PATENT DOCUMENTS

| | | | |
|---|---|---|---|
| EP | 4 047 006 A1 | 8/2022 | |
| JP | 2000-502901 A | 3/2000 | |
| JP | 2003-530838 A | 10/2003 | |
| JP | 2005-514060 A | 5/2005 | |
| JP | 2008-518615 A | 6/2008 | |
| JP | 2013-501036 A | 1/2013 | |
| JP | 2013-518038 A | 5/2013 | |
| JP | 2019-500390 A | 1/2019 | |
| WO | WO 01/79258 A1 | 10/2001 | |
| WO | WO 03/060071 A2 | 7/2003 | |
| WO | WO 2006/048777 A2 | 5/2006 | |
| WO | WO 2011/015649 A1 | 2/2011 | |
| WO | WO 2011/089255 A1 | 7/2011 | |
| WO | WO 2017/154869 A1 | 9/2017 | |
| WO | WO 2017/159540 A1 | 9/2017 | |
| WO | WO 2019/049967 A1 | 3/2019 | |

OTHER PUBLICATIONS

Drumm et al, Genetic Variation and Clinical Heterogeneity in Cystic Fibrosis, Annu. Rev. Pathol. Mech. Dis., 2012, 7, pp. 267-282 (Year: 2012).*
Yampolsky et al, The Exchangeability of Amino Acids in Proteins, Genetics, 2005, 170, pp. 1459-1472. (Year: 2005).*
International Search Report issued Dec. 22, 2020 in PCT/JP2020/040560 filed on Oct. 29, 2020, 2 pages.

* cited by examiner

*Primary Examiner* — Julie Ha
*Assistant Examiner* — Kristina M Hellman
(74) *Attorney, Agent, or Firm* — Oblon, McClelland, Maier & Neustadt, L.L.P.

(57) ABSTRACT
An aqueous pharmaceutical composition containing 10-100 mg/mL of a fusion protein of human serum albumin and human growth hormone, 10-150 mg/mL of sucrose, 0.15-10 mg/mL of a nonionic surfactant, 0.5-12 mg/mL of a preservative, and 1-30 mM of a buffer is, and the pH of the composition is 5.0-8.0.

1 Claim, 2 Drawing Sheets

Specification includes a Sequence Listing.

AQUEOUS PHARMACEUTICAL COMPOSITION CONTAINING FUSION PROTEIN OF SERUM ALBUMIN AND GROWTH HORMONE

CROSS-REFERENCE TO RELATED APPLICATIONS

The present application is a 35 U.S.C. § 371 national stage patent application of International patent application PCT/ JP2020/040560, filed on Oct. 29, 2020, which is based on and claims the benefits of priority to Japanese Application No. 2019-197978, filed on Oct. 30, 2019. The entire contents of these applications are incorporated herein by reference.

TECHNICAL FIELD

The present invention relates to an aqueous pharmaceutical composition of a medicine containing a fusion protein of serum albumin and growth hormone as an active ingredient, the aqueous pharmaceutical composition being storage-stable in a solution state, and more particularly, the invention relates to an aqueous pharmaceutical composition further containing sucrose and a nonionic surfactant as stabilizers.

BACKGROUND ART

Human growth hormone (hGH) is a protein secreted from the anterior pituitary gland under the control of the hypothalamus. hGH exhibits growth-promoting activity such as cartilage formation promotion and protein anabolism promotion, as well as body composition and lipid metabolism improving action. A child with low hGH secretion develops growth hormone deficiency dwarfism, which causes the child to exhibit short stature compared with a healthy child.

Preparations containing, as an active ingredient, a hGH (hGH preparations) having a molecular weight of about 22 kD produced as a recombinant protein by using hGH gene-introduced *Escherichia coli* have been clinically widely used as therapeutic agents for growth hormone deficiency dwarfism, short stature associated with Turner syndrome, Small-for-Gestational Age (SGA) dwarfism, dwarfism associated with Noonan syndrome, dwarfism caused by chronic renal failure, dwarfism associated with Prader-Willi syndrome, and dwarfism associated with cartilage dystrophy. hGH preparations are particularly effective in a case where these diseases are not accompanied by epiphyseal closure. hGH preparations are administered subcutaneously or intramuscularly to circulate in the blood and provide an effect of promoting the growth of a patient by the growth promoting activity of the hGH preparations. Furthermore, hGH preparations are widely clinically applied as a therapeutic agent for adult growth hormone deficiency. In patients with adult growth hormone deficiency, various abnormalities such as abnormal lipid metabolism are observed; however, when an hGH preparation is administered, the QOL of the patient is improved, such as that the patient's lipid metabolism is normalized. As an hGH preparation for growth hormone deficiency dwarfism, adult growth hormone deficiency, and the like, for example, GROWJECT (registered trademark) is available.

The half-life of hGH in blood plasma is considered to be less than 20 minutes, and hGH administered to a patient rapidly disappears from the blood. Therefore, in order to have the efficacy of hGH substantially exhibited in a patient, it is necessary to administer hGH to the patient intramuscularly three times a week or subcutaneously daily. Such frequent administration poses a burden on patients. Therefore, when it is possible to reduce the frequency of administration of hGH to a patient by increasing the stability of hGH in blood plasma and prolonging the half-life, the burden on the patient can be reduced, which is preferable.

Human serum albumin (HSA) is a protein whose mature form consists of 585 amino acids. HSA is a component that is most abundant among plasma proteins, and the half-life in blood plasma is as long as 14 to 20 days. HSA contributes to the regulation of plasma osmotic pressure and has a function of binding to cations, fatty acids, hormones, bilirubin, and other endogenous substances in the blood as well as exogenous substances such as drugs and transporting them. Generally, a substance bound to HSA is less likely to be taken up by organs and can circulate in the blood for a long period of time.

It is known that there are some of natural variants of human serum albumin (HSA). Human serum albumin Redhill is one of them (Non-Patent Documents 1 and 2). Human serum albumin Redhill is different, as compared to the amino acid sequence of the above-described normal human serum albumin consisting of 585 amino acids, from the viewpoint that the $320^{th}$ amino acid residue from the N-terminal side of human serum albumin Redhill is threonine instead of alanine and one arginine residue is added to the N-terminus thereof, so that human serum albumin Redhill consists of 586 amino acids. Due to the change from alanine to threonine, a sequence represented by Asn-Tyr-Thr is produced in the amino acid sequence of albumin Redhill, and the Asn (asparagine) residue in this sequence is N-linked glycosidated. Therefore, albumin Redhill is observed to have a molecular weight that is larger by about 2.5 kDa compared with the above-described normal human serum albumin.

Methods of increasing the stability of hGH in blood plasma by linking hGH to HSA have been reported (Patent Documents 1 to 8). A protein obtained by linking HSA to hGH is produced as a recombinant protein in a medium or in cells, by producing a transformed cell into which an expression vector incorporating a DNA in which a gene encoding hGH and a gene encoding HSA are linked in-frame is introduced and culturing this cell.

CITATION LIST

Patent Documents

Patent Document 1: WO 2017/154869
Patent Document 2: WO 2017/159540
Patent Document 3: JP 2003-530838 A
Patent Document 4: JP 2005-514060 A
Patent Document 5: JP 2000-502901 A
Patent Document 6: JP 2008-518615 A
Patent Document 7: JP 2013-501036 A
Patent Document 8: JP 2013-518038 A

DISCLOSURE OF THE INVENTION

Problem to be Solved by the Invention

Under the above-described circumstances, an object of the present invention is to provide an aqueous pharmaceutical composition of a medicine containing a fusion protein of human albumin and human growth hormone as an active ingredient, the aqueous pharmaceutical composition being stable to the extent that the aqueous pharmaceutical composition can be distributed in the market.

Means for Solving Problem

The inventors of the present invention repeatedly conducted a thorough investigation in a study directed to the above-described object, and as a result, the inventors found that a compound (human serum albumin mutant-hGH fusion protein) obtained by linking a mutant. (human serum albumin mutant) comprising, as compared with normal human serum albumin consisting of 585 amino acids, an amino acid sequence in which alanine as the $320^{th}$ amino acid residue from the N-terminus of normal human serum albumin has been substituted with threonine, to human growth hormone (hGH), is stable in an aqueous pharmaceutical composition containing sucrose and a nonionic surfactant. Thus, the inventors completed the present invention. That is, the present invention includes the following.

1. An aqueous pharmaceutical composition containing a fusion protein of human serum albumin and human growth hormone as an active ingredient, wherein the concentration of the fusion protein is 10 to 100 mg/mL, the concentration of sucrose is 10 to 150 mg/mL, the concentration of a nonionic surfactant is 0.15 to 10 mg/mL, the concentration of an antiseptic agent is 0.5 to 12 mg/mL, the concentration of a buffering agent is 1 to 30 mM, and pH is 5.0 to 8.0.
2. The aqueous pharmaceutical composition according to the above-described item 1, wherein the concentration of the fusion protein is 15 to 70 mg/mL.
3. The aqueous pharmaceutical composition according to the above-described item 1 or 2, wherein the concentration of the sucrose is 50 to 100 mg/mL.
4. The aqueous pharmaceutical composition according to any one of the above-described items 1 to 3, wherein the concentration of the nonionic surface is 1.5 to 4.5 mg/mL.
5. The aqueous pharmaceutical composition according to any one of the above-described items 1 to 4, wherein the nonionic surfactant is polysorbate or poloxamer.
6. The aqueous pharmaceutical composition according to any one of the above-described items 1 to 4, wherein the nonionic surfactant is selected from the group consisting of polysorbate 20, polysorbate 80, and polyoxyethylene (160) polyoxypropylene (30) glycol.
7. The aqueous pharmaceutical composition according to any one of the above-described items 1 to 6, wherein the antiseptic agent is phenol.
8. The aqueous pharmaceutical composition according to the above-described item 7, wherein the concentration of the phenol is 3 to 9 mg/mL.
9. The aqueous pharmaceutical composition according to any one of the above-described items 1 to 8, wherein the buffering agent is a phosphate buffering agent.
10. The aqueous pharmaceutical composition according to the above-described item 9, wherein the concentration of the phosphate buffering agent is 2 to 20 mM.
11. The aqueous pharmaceutical composition according to any one of the above-described items 1 to 10, wherein the pH is 6.0 to 7.8.
12. The aqueous pharmaceutical composition according to any one of the above-described items 1 to 10, wherein the pH is 6.5 to 7.6.
13. The aqueous pharmaceutical composition according to the above-described item 1, wherein the concentration of the fusion protein is 10 to 100 mg/mL, the concentration of the sucrose is 75 mg/mL, the nonionic surfactant is polyoxyethylene (160) polyoxypropylene (30) glycol, the concentration of the polyoxyethylene (160) polyoxypropylene (30) glycol is 3 mg/mL, the antiseptic agent is phenol, the concentration of the phenol is 6 mg/mL, the buffering agent is a phosphate buffering agent, the concentration of the phosphate buffering agent is 10 mM, and the pH is 7.0 to 7.4.
14. The aqueous pharmaceutical composition according to the above-described item 1, wherein the concentration of the fusion protein is 15 to 70 mg/mL, the concentration of the sucrose is 75 mg/mL, the nonionic surfactant is polyoxyethylene (160) polyoxypropylene (30) glycol, the concentration of the polyoxyethylene (160) polyoxypropylene (30) glycol is 3 mg/mL, the antiseptic agent is phenol, the concentration of the phenol is 6 mg/mL, the buffering agent is a phosphate buffering agent, the concentration of the phosphate buffering agent is 10 mM, and the pH is 7.0 to 7.4.
15. The aqueous pharmaceutical composition according to the above-described item 1, wherein the concentration of the fusion protein is 50 mg/mL, the concentration of the sucrose is 75 mg/mL, the nonionic surfactant is polyoxyethylene (160) polyoxypropylene (30) glycol, the concentration of the polyoxyethylene (160) polyoxypropylene (30) glycol is 3 mg/mL, the antiseptic agent is phenol, the concentration of the phenol is 6 mg/mL, the buffering agent is a phosphate buffering agent, the concentration of the phosphate buffering agent is 10 mM, and the pH is 7.0 to 7.4.
16. The aqueous pharmaceutical composition according to any one of the above-described items 1 to 15, wherein the amino acid sequence of the fusion protein has an identity of 85% or higher with an amino acid sequence set forth in SEQ ID NO:11.
17. The aqueous pharmaceutical composition according to any one of the above-described items 1 to 15, wherein the amino acid sequence of the fusion protein has an identity of 90% or higher with the amino acid sequence set forth in SEQ ID NO:11.
18. The aqueous pharmaceutical composition according to any one of the above-described items 1 to 15, wherein the amino acid sequence of the fusion protein has an identity of 95% or higher with the amino acid sequence set forth in SEQ ID NO:11.
19. The aqueous pharmaceutical composition according to any one of the above-described items 1 to 15, wherein the amino acid sequence of the fusion protein has the amino acid sequence set forth in SEQ ID NO:11.

Effect of the Invention

According to the present invention, for example, a medicine containing a protein in which human albumin and human growth hormone are linked as an active ingredient can be produced into an aqueous pharmaceutical composition that is stable to the extent that the aqueous pharmaceutical composition can be distributed in the market.

MODE(S) FOR CARRYING OUT THE INVENTION

Figure 1:
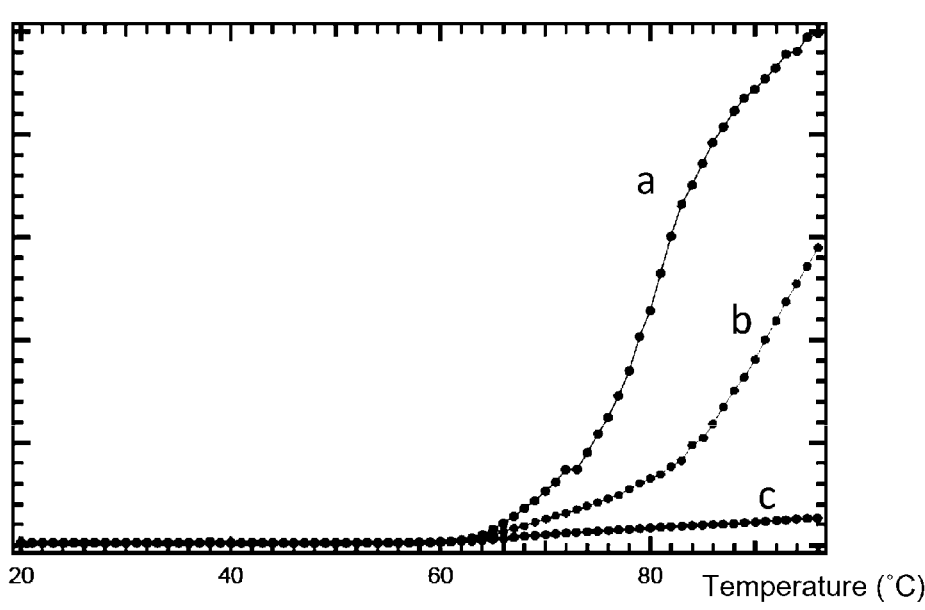
FIG. 1 is a diagram illustrating the results of measuring the static light scattering intensity in the Examples. The axis of ordinate represents the static light scattering intensity (arbitrary unit) at 473 nm, and the axis of abscissa represents temperature. In the diagram, (a), (b), and (c) indicate the measurement results for formulations 2-1, 2-2, and 2-3, respectively.

According to the present specification, when the term "human serum albumin" or "HSA" is simply used, this also includes, in addition to the normal wild-type human serum albumin consisting of 585 amino acid residues shown in SEQ ID NO:1, a mutant of HSA corresponding to an amino acid sequence set forth in SEQ ID NO:1, in which one amino acid residue or a plurality of amino acid residues have been substituted, deleted, and/or added (according to the present specification, the "addition" of an amino acid residue means addition of a residue at a terminus or the inner part of the sequence), without particular discrimination as long as the mutant has functions as normal wild-type human serum albumin, such as a function of binding to endogenous substances in the blood and exogenous substances such as drugs and transporting them. In the case of substituting an amino acid residue with another amino acid residue, the number of amino acid residues to be substituted is preferably 1 to 10, more preferably 1 to 5, and even more preferably 1 to 3. In the case of deleting an amino acid residue, the number of amino acid residues to be deleted is preferably 1 to 10, more preferably 1 to 5, and even more preferably 1 to 3. For example, a mutant consisting of 584 amino acid residues, in which an amino acid residue at the N-terminus or C-terminus of the amino acid sequence set forth in SEQ ID NO:1 has been deleted, is also included in human serum albumin. Furthermore, substitution and deletion of these amino acid residues may be combined. Furthermore, a sequence in which one amino acid residue or a plurality of amino acid residues have been added into the amino acid sequence of normal wild-type HSA or a mutant thereof, or at the N-terminal side or C-terminal side of the amino acid sequence, is also acceptable. The number of amino acid residues to be added at this time is preferably 1 to 10, more preferably 1 to 5, and even more preferably 1 to 3.

Regarding a mutant of HSA into which a combination of at least two kinds of mutations among these three kinds of mutations, namely, substitution, deletion, and addition of amino acids, has been introduced, it is preferable that the mutant has an amino acid sequence obtained by performing deletion of 0 to 10 amino acid residues, substitution of 0 to 10 amino acid residues with other amino acid residues, and addition of 0 to 10 amino acid residues, with respect to the amino acid sequence set forth in SEQ ID NO:1. More preferably, the number of those amino acid residues to be subjected to each of those deletion, substitution, and/or addition with respect to the amino acid sequence set forth in SEQ ID NO:1 is preferably 5 or less, and more preferably 3 or less.

According to the present invention, the term "human serum albumin Redhill" (HSA-Redhill) means a variant of human serum albumin, which consists of 586 amino acid residues as set forth in SEQ ID NO:2. Human serum albumin Redhill corresponds to a product in which, with regard to the amino acid sequence of wild-type human serum albumin consisting of 585 amino acids as set forth in SEQ ID NO:1, the $320^{th}$ amino acid residue from the N-terminus is threonine instead of alanine, and one arginine residue has been added to the N-terminus. Due to this substitution of alanine with threonine, a sequence portion represented by Asn-Tyr-Thr is produced in the amino acid sequence of albumin Redhill, and the Asn (asparagine) residue in this sequence portion is N-linked glycosidated. For this reason, albumin Redhill is observed to have a molecular weight larger by about 2.5 kDa compared with normal wild-type albumin (SEQ ID NO:1).

According to the present invention, the term "human serum albumin mutant" (HSA mutant) means the above-mentioned mutant for normal wild-type HSA (SEQ ID NO:1), provided that the mutant is other than the variant set forth in SEQ ID NO:2 (HSA-Redhill). A preferred HSA mutant according to the present invention includes, in addition to an amino acid sequence set forth in SEQ ID NO:3 in which the $320^{th}$ alanine from the N-terminus of the amino acid sequence of wild-type HSA has been substituted with, threonine, an amino acid sequence in which one amino acid residue or a plurality of amino acid residues in the amino acid sequence set forth in SEQ ID NO:3 have been substituted with other amino acid residues, deleted, or added, provided that the $318^{th}$ asparagine residue and the $320^{th}$ threonine residue from the N-terminus of the amino acid sequence set forth in SEQ ID NO:3 are conserved in a state of being coupled by a peptide bond, with a single amino acid residue (X) other than proline interposed between those two residues, as long as the amino acid sequence has the functions of normal wild-type human serum albumin, such as a function of binding to endogenous substances in the blood and exogenous substances such as drugs and transporting them. When an amino acid residue in the amino acid sequence is substituted with another amino acid residue, the number of amino acid residues to be substituted is preferably 1 to 10, more preferably 1 to 5, and even more preferably 1 to 3. In the case of deleting an amino acid residue, the number of amino acid residues to be deleted is preferably 1 to 10, more preferably 1 to 5, and even more preferably 1 to 3. For example, the HSA mutant may also be a mutant consisting of 584 amino acid residues, in which an amino acid residue at the N-terminus or C-terminus of the amino acid sequence set forth in SEQ ID NO:3 has been deleted. Furthermore, a combination of these substitutions and deletions of amino acid residues is also acceptable. In addition, products obtained by adding one amino acid residue or a plurality of amino acid residues into the amino acid sequences of those mutants or to the N-terminal side or the C-terminal side of the amino acid sequences, are also acceptable. That is, the HSA mutant may be a product in which a combination of at least two kinds of mutations among the three kinds of mutations, namely, substitution, deletion, and addition of amino acids, has been introduced into the amino acid sequence set forth in SEQ ID NO:3, and in which deletion of 0 to 10 amino acid residues, substitution of 0 to 10 amino acid residues with other amino acid residues, and addition of 0 to 10 amino acid residues have been carried out. However, the $318^{th}$ to $320^{th}$ amino acid residues from the N-terminus of the amino acid sequence set forth in SEQ ID NO:3 must be asparagine-Y-threonine ("X" is an amino acid residue other than proline), and the sequence is asparagine-tyrosine-threonine. Incidentally, the human serum albumin mutant is included in human serum albumin as long as the mutant retains the functions as human serum albumin. Here, the amino acid sequence of the human serum albumin mutant preferably has an identity of 85% or higher, more preferably an identity of 90% or higher, and even more preferably an identity of 95% or higher, with the amino acid sequence of normal wild-type HSA set forth in SEQ ID NO:1.

According to the present invention, the position of each mutation and the form thereof (deletion, substitution, or addition) in each of various HSA mutants as compared with normal wild-type HSA can be easily checked by checking the alignment of the amino acid sequences of the two HSAs. According to the present invention, the identity between the amino acid sequence of wild-type HSA and the amino acid sequence of HSA to which mutation has been applied, can be easily calculated by using well-known homology calculation algorithms. Examples of such algorithms include BLAST (Altschul S F. J Mol. Biol., 215, 403-10 (1990)), the similarity search method of Pearson and Lipman (Proc. Natl. Acad. Sci., USA, 85, 2444 (1988)), and the local homology algorithm of Smith and Waterman (Adv. Appl. Math., 2, 482-9 (1981)).

The substitution of an amino acid in the above-described amino acid sequence of HSA with another amino acid occurs, for example, within a family of amino acids that are relevant in terms of the side chains and chemical characteristics of those amino acids. Such substitution within a family of amino acids is not expected to bring significant changes in the functions of HSA (that is, conservative amino acid substitution). Examples of such a family of amino acids include the following:

(1) aspartic acid and glutamic acid, which are acidic amino acids, (2) histidine, lysine, and arginine, which are basic amino acids, (3) phenylalanine, tyrosine, and tryptophan, which are aromatic amine acids, (4) serine and threonine, which are amino acids having a hydroxy group (hydroxyamino acids), (5) methionine, alanine, valine, leucine, and isoleucine, which are hydrophobic amino acids, (6) cysteine, serine, threonine, asparagine, and glutamine, which are neutral hydrophilic amino acids, (7) glycine and proline, which are amino acids affecting the alignment of peptide chains, (8) asparagine and glutamine, which are amide type amino acids (polar amino acids), (9) alanine, leucine, isoleucine, and valine, which are aliphatic amino acids,

(10) alanine, glycine, serine, and threonine, which are amino acids having a small side chain, and

(11) alanine and glycine, which are amino acids having a particularly small side chain.

A human serum albumin mutant in a protein in which human growth hormone and a human serum albumin mutant are linked (a typical example of HSA mutants) in the Examples that will be described below is different from the amino acid sequence of wild-type human serum albumin (SEQ ID NO:1) consisting of 585 amino acids, only in that the 320th amino acid residue from the N7-terminus is threonine instead of alanine (SEQ ID NO:3). Due to this difference, in this HSA mutant (referred to as "HSA (A320T)"), a sequence portion represented by Asn-Tyr-Thr is produced in the amino acid sequence, and the Asn (asparagine) residue in this sequence portion can be N-linked glycosidated.

According to the present specification, the term "fusion protein of human serum albumin and human growth hormone" or "human serum albumin-hGH fusion protein (HSA-hGH fusion protein)" refers to a protein in which HSA and growth hormone are linked. Here, when it is said that these proteins are "linked", for example, the term includes coupling these by means of a peptide bond; however, the term is not limited to this. Furthermore, when it is said that these proteins are "linked", not only direct coupling between the N-terminus of one protein and the C-terminus of the other protein with a peptide bond, but also indirectly linking the two proteins via a linker, are also included. Particularly, when human serum albumin is a human serum albumin mutant, this is referred to as "fusion protein of a human serum albumin mutant and human growth hormone" or "human serum albumin mutant-hGH fusion protein (HSA mutant-hGH fusion protein)". That is, the human serum albumin mutant-hGH fusion protein is included in the human serum albumin-hGH fusion protein. The "fusion protein of human serum albumin and human growth hormone" can also be referred to as HSA-coupled hGH.

Here, the "linker" is a structural part that links the above-described two polypeptides by covalent bonding between the two polypeptides, and the linker is derived from neither of the ends of HSA (including an HSA mutant) and growth hormone as the bonding partner. The linker can be a single amino acid residue or a peptide chain moiety (peptide linker) consisting of two or more amino acid residues, both being linked by a peptide bond to the two polypeptides, and these linkers each consisting of one or more amino acid residues are comprehensively referred to as "Peptide linker" in the present specification. Furthermore, according to the present specification, when it is said that HSA and growth hormone are linked "through a peptide bond", this includes the case where the two are directly linked by a peptide bond, and the case where the two are linked by linkage to a peptide linker. Incidentally, in the present specification, when HSA and growth hormone are linked directly or through a peptide linker, the compound "human serum albumin-hGH fusion protein (HSA-hGH fusion protein)" can also be said to be "human serum albumin-fused hGH (HSA-fused hGH)". The same also applies to human serum albumin mutant-hGH fusion protein (HSA mutant-hGH fusion protein).

According to the present invention, when HSA and growth hormone are linked via a peptide linker, the linker is preferably composed of 1 to 50, more preferably 1 to 17, even more preferably 1 to 10, and still more preferably 1 to 6, amino acid residues, and for example, the linker composed of 2 to 17, 2 to 10, 10 to 40, 20 to 34, 23 to 31, or 25 to 29, amino acids, while for example, the linker is composed of only one amino acid residue or composed of 2, 3, 5, 6, or 20 amino acid residues. The amino acid residue or amino acid sequence constituting the peptide linker is not limited as long as the HSA moiety linked by the peptide linker retains the functions as HSA, and the growth hormone moiety can also exhibit the physiological activity of growth hormone under physiological conditions; however, it is preferable that the peptide linker is composed of glycine and serine. Suitable examples of the peptide linker include peptide linkers consisting of one glycine, one serine, Gly-Ser, Gly-Gly-Ser, Gly-Gly-Gly-Gly-Ser (SEQ ID NO:4), Gly-Gly-Gly-Gly-Gly-Ser (SEQ ID NO:5), and Ser-Gly-Gly-Gly-Gly-Gly (SEQ ID NO:6); as well as peptide linkers including these amino acid sequences. A peptide linker having a sequence including any one kind of these amino acid sequences, which is repeated 2 to 10 times or 2 to 5 times consecutively, can also be suitably used as the peptide linker, and a peptide linker having a sequence including any two or more kinds of these amino acid sequences in combination, which are repeated 1 to 10 times or 2 to 5 times consecutively, can also be suitably used as the peptide linker. A suitable example of a peptide linker having any two or more kinds of these amino acid sequences in combination may be a peptide linker that includes an amino acid sequence having a total of 20 amino acids, composed of the amino acid sequence Gly-Ser followed by three consecutive repetitions of the amino acid sequence Gly-Gly-Gly-Gly-Gly-Ser (SEQ ID NO:5).

Regarding a method of linking two different polypeptides, for example, a method of producing an expression vector having a DNA incorporated therein, the DNA being a DNA in which a gene encoding one of the polypeptides is linked in-frame downstream of a gene encoding the other polypeptide, and culturing a host cell that has been transformed by using this expression vector to express the expression vector as a recombinant fusion protein, is general and can be utilized in the present invention.

When the HSA-hGH fusion protein is produced by expressing the fusion protein as a recombinant in a transformed cell, a fusion protein in the form in which a polypeptide including the amino acid sequence of growth hormone is linked to either the N-terminus or the C-terminus of a polypeptide including the amino acid sequence of HSA is obtained. An HSA-hGH fusion protein produced by using the gene recombination technology is particularly referred to as recombinant HSA-hGH fusion protein.

When the polypeptide including the amino acid sequence of growth hormone is linked to the N-terminal side of the polypeptide including the amino acid sequence of HSA, an expression vector having a DNA incorporated therein, the DNA being a DNA in which a gene encoding the polypeptide that includes the amino acid sequence of HSA is linked in-frame downstream of a gene encoding the polypeptide that includes the amino acid sequence of growth hormone, is used. When the two polypeptides are indirectly linked through a peptide linker, a DNA sequence encoding the linker is inserted in-frame between the genes encoding the two polypeptides.

When the polypeptide including the amino acid sequence of growth hormone is linked to the C-terminal side of the polypeptide including the amino acid sequence of HSA, an expression vector having a DNA incorporated therein, the DNA being a DNA in which a gene encoding the polypeptide that includes the amino acid sequence of HSA is linked in-frame upstream of a gene encoding the polypeptide that includes the amino acid sequence of growth hormone, is used. When the two polypeptides are indirectly linked through a peptide linker, a DNA sequence encoding the linker is inserted in-frame between the genes encoding the two polypeptides.

In order to produce the HSA-hGH fusion protein in a host cell, an expression vector in which a DNA encoding any one of those is incorporated is introduced into the host cell. The host cell that can be used for this purpose is not particularly limited as long as the host cell can express the HSA-hGH fusion protein when such an expression vector is introduced therein, and the host cell may be any one of eukaryotic cells such as a mammalian cell, yeast, a plant cell, and an insect cell; and prokaryotic cells such as *Escherichia coli* and *Bacillus subtilis*; however, a mammalian cell is particularly suitable. However, the host cell in the case of expressing as a sugar chain-modified protein is selected from eukaryotic cells such as a mammalian cell, yeast, a plant cell, and an insect cell. The Asn residue of a sequence portion represented by Asn-Tyr-Thr, which is produced when the $320^{th}$ amino acid residue of normal wild-type HSA is converted to threonine, or the Asn residue in a sequence represented by Asn-X-Thr ("X" is an amino acid residue other than proline) is N-linked glycosidated by performing the expression of the HSA-hGH fusion protein in a eukaryotic cell.

When a mammalian cell is used as the host cell, the type of this mammalian cell is not particularly limited; however, a cell derived from human, mouse, or Chinese hamster is preferred, and Chinese hamster ovarian cell-derived CHO cell, or mouse myeloma-derived NS/0 cell is preferred. Furthermore, regarding the expression vector that is used at this time in order to incorporate and express a DNA fragment encoding the HSA-hGH fusion protein, any expression vector that brings expression of the gene when introduced into a mammalian cell can be used without particular limitation. The gene incorporated into the expression vector is disposed downstream of a DNA sequence (gene expression control site) capable of regulating the frequency of gene transcription in a mammalian cell. Examples of the gene expression control site that can be used for the present invention include a cytomegalovirus-derived promoter, an SV40 early promoter, a human elongation factor-1α (EF-1α) promoter, and a human ubiquitin C promoter.

Mammalian cells into which such an expression vector has been introduced will express the protein incorporated in the expression vector; however, the amount of expression thereof may vary from individual cell to individual cell and may not be uniform. Therefore, in order to efficiently produce the HSA-hGH fusion protein, a step of selecting these cells having high expression levels from the mammalian cells into which the expression vector has been introduced is necessary. In order to carry out this selection step, a gene working as a selectable marker is incorporated into the expression vector.

A most general selectable marker is an enzyme that degrades drugs such as puromycin and neomycin (drug resistance marker). Mammalian cells usually die out in the presence of these drugs at or above certain concentrations. However, mammalian cells into which an expression vector having a drug resistance marker gene incorporated therein has been introduced, can survive even in the presence of the above-described drugs because the drugs can be detoxified or attenuated by the expressed drug resistance marker. When an expression vector having a drug resistance marker incorporated therein as the selectable marker is introduced into mammalian cells, and culture is continued in a selective medium containing the drug corresponding to the drug resistance marker, for example, while gradually increasing the concentration of the drug, a cell that can proliferate even in the presence of a higher concentration of the drug is obtained. In the cells selected in this manner, the amount of expression of a gene encoding a target protein, which has been incorporated into an expression vector, is generally increased together with the drug resistance marker, and as a result, cells having a high expression level of the protein are selected.

Furthermore, glutamine synthetase (GS) can also be used as the selectable marker. Glutamine synthetase is an enzyme that synthesizes glutamine from glutamic acid and ammonia. When mammalian cells are cultured in a selective medium that contains an inhibitor of glutamine synthetase, for example, L-methionine sulfoximine (MSX), and does not contain glutamine, the cells usually die out. However, when an expression vector in which glutamine synthetase has been incorporated as the selectable marker is introduced into mammalian cells, the expression level of glutamine synthetase is increased in the cells, and therefore, the cells can proliferate even in the presence of a higher concentration of MSX. At this time, when culture is continued while gradually increasing the concentration of MSX, cells capable of proliferating even in the presence of a higher concentration of MSX are obtained. In the cells selected in this manner, the amount of expression of a gene encoding a target protein, which has been incorporated into an expression vector, is generally increased together with the glutamine synthetase, and as a result, cells having a high expression level of the protein are selected.

Furthermore, dihydrofolate reductase (DHFR) can also be used as the selectable marker. When DHFR is used as the selectable marker, mammalian cells into which the expression vector has been introduced are cultured in a selective medium containing a DHFR inhibitor such as methotrexate or aminopterin. When culture is continued while gradually increasing the concentration of the DHFR inhibitor, cells capable of proliferating even in the presence of a higher concentration of the DHFR inhibitor are obtained. It is preferable that the selective medium to be used at this time does not contain hypoxanthine and thymidine. In the cells selected in this manner, the amount of expression of a gene encoding a target protein, which has been incorporated into an expression vector, is generally increased together with DHFR, and as a result, cells having a high expression level of the protein are selected.

Expression vectors in which glutamine synthetase (GS) as a selectable marker is disposed downstream of a gene encoding a target protein, with an internal ribosome entry site (IRES) interposed therebetween, are known (WO 2012/063799 and WO 2013/161958). The expression vectors described in these documents can be particularly suitably used for the production of the HSA-hGH fusion protein.

For example, an expression vector for expressing a target protein, the expression vector including a first gene expression control site, a gene encoding the protein downstream thereof, an internal ribosome entry site further downstream, and a gene encoding glutamine synthetase even further downstream, and the expression vector further including dihydrofolate reductase gene or a drug resistance gene downstream of the first gene expression control site or a second gene expression control site different from this first gene expression control site, can be suitably used for the production of the HSA-hGH fusion protein. With regard to this expression vector, as the first gene expression control site or the second gene expression control site, a cytomegalovirus-derived promoter, an SV40 early promoter, a human elongation factor-1α promoter (hEF-1α promoter), and a human ubiquitin C promoter are suitably used; however, a hEF-1α promoter is particularly suitable.

Furthermore, regarding the internal ribosome entry site, such a site derived from a 5'-untranslated region of the genome of a virus selected from the group consisting of a virus of the family Picornavirus, foot-and-mouth disease virus, hepatitis A virus, hepatitis C virus, a coronavirus, bovine enterovirus, Theiler's murine encephalomyelitis virus, and Coxsackie B virus, or a gene selected from the group consisting of human immunoglobulin heavy chain binding protein, *Drosophila* Antennapedia gene, and *Drosophila* Ultrabithorax gene, is suitably used; however, an internal ribosome entry site derived from the 5'-untranslated region of the mouse encephalomyelitis virus genome is particularly suitable. When an internal ribosome entry site derived from the 5'-untranslated region of the mouse encephalomyelitis virus genome is used, the wild-type internal ribosome entry site as well as an internal ribosome entry site in which some of a plurality of start codons included in the wild-type internal ribosome entry site have been destroyed, can also be suitably used. Furthermore, a drug resistance gene that is suitably used for this expression vector is preferably the puromycin or neomycin resistance gene, and more preferably the puromycin resistance gene.

Furthermore, for example, an expression vector for expressing a target protein, the expression vector including a human elongation factor-1α promoter, a gene encoding the protein downstream thereof, an internal ribosome entry site derived from a 5'-untranslated region of the mouse encephalomyelitis virus genome further downstream, and a gene encoding glutamine synthetase even further downstream, and further including another gene expression control site and dihydrofolate reductase gene downstream thereof, in which the internal ribosome entry site is an internal ribosome entry site in which some of a plurality of start codons included in the wild-type internal ribosome entry site have been destroyed, can be suitably used for the production of the HSA-hGH fusion protein. Examples of such an expression vector include the expression vector described in WO 2013/161958.

Furthermore, for example, an expression vector for expressing a target protein, the expression vector including a human elongation factor-1α promoter, a gene encoding the protein downstream thereof, an internal ribosome entry site derived from a 5'-untranslated region of the mouse encephalomyelitis virus genome further downstream, and a gene encoding glutamine synthetase even further downstream, and further including another gene expression control site and a drug resistance gene downstream thereof, in which the internal ribosome entry site is an internal ribosome entry site in which some of a plurality of start codons included in the wild-type internal ribosome entry site have been destroyed, can be suitably used for the production of the HSA-hGH fusion protein. Examples of such an expression vector include pE-mIRES-GS-puro described in WO 2012/063799 and pE-mIRES-GS-mNeo described in WO 2013/161958.

At the 3'-terminus of the internal ribosome entry site derived from the 5'-untranslated region of the wild-type mouse encephalomyelitis virus genome, there are three start codons (ATG), and the sequence portion including the three start codons is set forth in SEQ ID NO:7 (5'-ATGataatATGgccacaaccATG-3': ATG of the start codon is indicated with capital letters). As an internal ribosome entry site in which some of the start codons in this sequence portion have been destroyed, for example, there is a sequence set forth in SEQ ID NO:8 (5'-atgataagcttgccacaaccatg-3'), and the above-described pE-mIRES-GS-puro and pE-mIRES-GS-mNeo are expression vectors having IRES including the sequence set forth in SEQ ID NO:8.

According to the present invention, a mammalian cells into which an expression vector having a DNA fragment encoding the HSA-hGH fusion protein has been introduced, are selectively cultured in a selectable medium in order to select cells having high expression levels of these proteins.

When DHFR is used as the selectable marker in selective culture, the concentration of a DHFR inhibitor included in the selective medium is increased stepwise. When the DHFR inhibitor is methotrexate, the maximum concentration thereof is preferably 0.25 to 5 µM, more preferably 0.5 to 1.5 µM, and even more preferably about 1.0 µM.

When GS is used as the selectable marker, the concentration of a GS inhibitor included in the selective medium is increased stepwise. When the GS inhibitor is MSX, the maximum concentration thereof is preferably 10 to 1000 µM or the like, and for example, the maximum concentration is 20 to 500 μM, 20 to 80 μM, or 20 to 30 μM. Furthermore, at this time, a medium that does not contain glutamine is generally used as the selective medium.

When an enzyme that degrades puromycin is used as a selectable marker, the maximum concentration of puromycin included in the selectable marker is preferably 3 to 30 μg/mL, more preferably 5 to 20 μg/mL, and even more preferably about 10 μg/mL.

When an enzyme that degrades neomycin is used as a selectable marker, the maximum concentration of G418 included in the selective medium is preferably 0.1 to 2 mg/mL, more preferably 0.5 to 1.5 mg/mL, and even more preferably about 1 mg/mL.

Furthermore, regarding the medium for culturing mammalian cells, any medium capable of culturing and proliferating mammalian cells can be used without particular limitation, together with a medium that is used for selective culture and a medium that is used for producing a recombinant protein (medium for recombinant protein production), which will be described below; however, a serum-free medium is preferably used. Since HSA has a property of adsorbing the components included in blood serum, when HSA is produced by using a medium containing blood serum, HSA that has adsorbed impurities in the blood serum is obtained, and therefore, it is necessary to remove these impurities in a subsequent step.

According to the present invention, the HSA-hGH fusion protein is particularly a fusion protein obtainable by culturing cells expressing these in a serum-free medium. Since the amount of adsorption of impurities to the HSA-hGH fusion protein can be reduced by using a serum-free medium, the subsequent purification steps can be simplified.

Cells selected by selective culture and having a high expression level of the HSA-hGH fusion protein are used for the production of the HSA-hGH fusion protein (HSA-hGH fusion protein producing cells). The production of the HSA-hGH fusion protein is carried out by culturing the HSA-hGH fusion protein producing cells in a medium for HSA-hGH fusion protein production. This culture is referred to as production culture.

According to the present invention, as the serum-free medium to be used as the medium for HSA-hGH fusion protein production, for example, a medium containing 3 to 700 mg/L of amino acids, 0.001 to 50 mg/L of vitamins, 0.3 to 10 g/L of polysaccharides, 0.1 to 10000 mg/L of inorganic salts, 0.001 to 0.1 mg/L of trace elements, 0.1 to 50 mg/L of nucleoside, 0.001 to 10 mg/L of fatty acids, 0.01 to 1 mg/L of biotin, 0.1 to 20 μg/L of hydrocortisone, 0.1 to 20 mg/L of insulin, 0.1 to 10 mg/L of vitamin B12, 0.01 to 1 mg/L of putrescine, 10 to 500 mg/L of sodium pyruvate, and water-soluble iron compounds is suitably used. If desired, thymidine, hypoxanthine, a conventional pH indicator, an antibiotic substance, and the like may also be added to the medium.

Regarding the serum-free medium to be used as the medium for HSA-hGH fusion protein production, DMEM/F12 medium (mixed medium of DMEM and F12) may be used as a basic medium, and these media are respectively well known to those ordinarily skilled in the art. Furthermore, DMEM (HG) HAM modified (R5) medium, which includes sodium hydrogen carbonate, L-glutamine, D-glucose, insulin, sodium selenite, diaminobutane, hydrocortisone, iron(II) sulfate, asparagine, aspartic acid, serine, and polyvinyl alcohol, may also be used as the serum-free medium. In addition, a commercially available serum-free medium, for example, CD OPTICHO™ medium (protein-free and animal origin-free cell culture medium for highyield CHO cell growth), CHO-S-SFM II medium, or CD CHO medium (Thermo Fisher Scientific, Inc.), IS CHO-V™ medium (serum-free and animal-derived component-free medium) (FUJIFILM Irvine Scientific, Inc.), EX-CELL® 302 medium (serum-free liquid medium for a long-term growth of CHO cells), EX-CELL® R Advanced medium (animal component free and contains no hydrolysates), or EX-CELL® 325-PF medium (protein-free, animal content free medium for growth of CHO cells) (SAFC Biosciences, Inc.), and the like can also be used as basic media.

To the medium for HSA-hGH fusion protein production, 1 to 50 g/L (for example, 1 to 5 g/L) of a hydrolysate derived from a plant such as soybean, wheat, or rice can be added as appropriate. A most generally used hydrolysate is a soybean-derived protein hydrolysate. However, the H-HSA-hGH fusion protein can be produced without adding a hydrolysate derived from a plant such as rice, for example, a soybean-derived protein hydrolysate, to the medium for HSA-hGH fusion protein production.

The culture fluid after completion of production culture is subjected to a chromatography step for purifying the HSA-hGH fusion protein. However, what is subjected to the chromatography step is a culture supernatant obtained by removing cells and the like from the culture fluid. Examples of a method of obtaining a culture supernatant from the culture fluid include filtration using a membrane filter and centrifugal separation.

According to the present invention, each of chromatography steps for purifying the HSA-hGH fusion protein may be carried out in the presence of a nonionic surfactant in order to prevent non-specific adsorption of proteins as necessary. There is no particular limitation on which nonionic surfactant should be used; however, a polysorbate-based surfactant is preferably used, and more preferred is polysorbate 80 or polysorbate 20. The concentration of such a nonionic surfactant is preferably 0.005% (w/v) to 0.1% (w/v), more preferably 0.005% (w/v) to 0.05% (w/v), and for example, 0.01% (w/v) or 0.05% (w/v).

A purification step for the HSA-hGH fusion protein can be carried out at room temperature or a low temperature; however, the purification step can be carried out preferably at a low temperature, particularly at 1° C. to 10° C.

According to an embodiment of the present invention, the purification step for the HSA-hGH fusion protein includes a column chromatography step of using a material to which an antibody having an affinity for the HSA-hGH fusion protein is linked, as a stationary phase; a column chromatography step of using a material having an affinity for phosphate group as a stationary phase; a cation exchange column chromatography step; and a size exclusion column chromatography step. However, one or a plurality of chromatography steps can also be added to these chromatography steps. Examples of such additional chromatography steps include a column chromatography step of using a material to which an antibody having an affinity for the HSA-hGH fusion protein is linked, as a stationary phase; a column chromatography step of using a material having an affinity for phosphate group as a stationary phase; a cation exchange column chromatography step; an anion exchange column chromatography step; a hydrophobic column chromatography step; a dye affinity column chromatography step; and a size exclusion column chromatography step.

According to an embodiment of the present invention, the purification step for the HSA-hGH fusion protein includes a column chromatography step of using a material to which an antibody having an affinity for the HSA-hGH fusion protein is linked, as a stationary phase; a column chromatography step of using a material having an affinity for phosphate group as a stationary phase; a cation exchange column chromatography step; and a size exclusion column chromatography step, in this order. However, one or a plurality of chromatography steps can also be added to these chromatography steps. Examples of such additional chromatography steps include a column chromatography step of using a material to which an antibody having an affinity for the HSA-hGH fusion protein is linked, as a stationary phase; a column chromatography step of using a material having an affinity for phosphate group as a stationary phase; a cation exchange column chromatography step; an anion exchange column chromatography step; a hydrophobic column chromatography step; a dye-ligand column chromatography step; and a size exclusion column chromatography step. The additional chromatography may be added between any adjacent steps or may be added as a first chromatography step or a final chromatography step.

The purification step according to an embodiment of the present invention, including a column chromatography step of using a material to which an antibody having an affinity for the HSA-hGH fusion protein is linked, as a stationary phase; a column chromatography step of using a material having an affinity for phosphate group as a stationary phase; a cation exchange column chromatography step; and a size exclusion column chromatography in this order will be described in detail below.

A first column chromatography step is to use column chromatography that uses a material to which an antibody having an affinity for the HSA-hGH fusion protein is linked, as a stationary phase. Here, the antibody may have an affinity for either HSA or hGH; however, an antibody having an affinity for hGH is preferred. For example, Capture select Human Growth Hormone Affinity Matrix (Thermo Fisher Scientific, Inc.), which includes a carrier to which an antibody to human growth hormone is linked, can be suitably used.

When column chromatography that uses a material to which an antibody having an affinity for hGH is linked, is used as a stationary phase, the HSA-hGH fusion protein is subjected to a column that has been equilibrated in advance with a buffer solution. Here, the type of the buffer solution is not particularly limited; however, a Tris-HCl buffer solution is preferred, and the concentration thereof is preferably 5 to 50 mM, and more preferably 10 to 30 mM. Furthermore, the pH is preferably adjusted to 6.7 to 7.3, more preferably to 6.9 to 7.1, and even more preferably to about 7.0. Elution of the HSA-hGH fusion protein from the column is preferably carried out using glycine-hydrochloric acid. The concentration of glycine-hydrochloric acid is preferably 20 to 100 mM, more preferably 40 to 60 mM, and even more preferably about 50 mM. Furthermore, the pH is preferably adjusted to 2.0 to 4.0, more preferably to 2.8 to 3.2, and even more preferably to about 3.0. The pH of the eluate is immediately adjusted to near neutrality, for example, pH 6.4 to 7.0.

A second column chromatography step is to use a material having an affinity for phosphate group as a stationary phase. As suitable examples of column chromatography using a material having an affinity for phosphate group as a stationary phase, hydroxyapatite column chromatography and fluorapatite column chromatography may be mentioned; however, hydroxyapatite column chromatography is particularly preferred. These are intended to remove contaminants by utilizing an interaction of both metal affinity by calcium ion and cation exchange by phosphate group.

The case of using hydroxyapatite column chromatography will be described in detail below. The carrier to be used for hydroxyapatite chromatography is not particularly limited and may be ceramic or crystalline; however, one of particularly preferred carriers may be CHT Type II, 40 μm (Bio-Rad Laboratories, Inc.).

With regard to the eluate obtained in the first column chromatography step, the pH and the conductivity are adjusted before the eluate is subjected to a hydroxyapatite chromatography column. At this time, the pH is preferably adjusted to 6.5 to 7.5, more preferably to 6.8 to 7.2, and even more preferably to 6.9 to 7.1. Furthermore, the conductivity is preferably adjusted to 0.4 to 0.8 S/m, and more preferably to 0.5 to 0.7 S/m.

The eluate whose pH and conductivity have been adjusted is subjected to the hydroxyapatite chromatography column that has been equilibrated in advance with a buffer solution. Here, the type of the buffer solution is not particularly limited; however, an MES buffer solution is preferred, while the concentration thereof is preferably 5 to 50 mM, more preferably 10 to 30 mM, and for example, 20 mM. Furthermore, the pH of the buffer solution is preferably adjusted to 6.7 to 7.3, more preferably to 6.9 to 7.1, and even more preferably to about 7.0. Furthermore, the buffer solution includes phosphate ions, and the concentration thereof is preferably 0 to 3 mM, more preferably 0 to 2 mM, and for example, 1 mM.

Elution of the HSA-hGH fusion protein from the hydroxyapatite chromatography column is carried out by using a buffer solution having an increased concentration of phosphate ion. The concentration of phosphate at this time is preferably 20 to 50 mM, more preferably 25 to 40 mM, even more preferably 25 to 35 mM, and for example, 30 mM.

A third column chromatography step is to use cation exchange column chromatography and is intended to remove contaminant proteins. There is no particular limitation on which cation exchange resin should be used for the cation exchange column chromatography; however, a weak cation exchange resin is preferred, and a weak cation exchange resin having selectivity based on both hydrophobic interaction and hydrogen bonding formation is more preferred. For example, a weak cation exchange resin having a phenyl group, an amide bond, and a carboxyl group and having selectivity based on hydrophobic interaction and hydrogen bonding formation, such as Capto MMC (GE Healthcare), can be suitably used.

With regard to the eluate obtained in the second column chromatography step, the pH and the conductivity are adjusted before the eluate is subjected to cation exchange column chromatography. At this time, the pH is preferably adjusted to 5.3 to 6.2, more preferably to 5.4 to 6.1, and even more preferably to 5.6 to 5.8. Furthermore, the conductivity is preferably adjusted to 0.5 to 0.9 S/m, and more preferably to 0.6 to 0.8 S/m.

The eluate whose pH and conductivity have been adjusted is subjected to cation exchange column chromatography that has been equilibrated in advance with a buffer solution. Here, the type of the buffer solution is not particularly limited; however, an MES buffer solution is preferable, and the concentration thereof is preferably 30 to 70 mM, more preferably 40 to 60 mM, and for example, 50 mM. Furthermore, the pH of the buffer solution is preferably adjusted to 5.4 to 6.0, more preferably to 5.6 to 5.8, and for example, to 5.7. Furthermore, the buffer solution includes a salt, and when the salt is a neutral salt, the concentration in the buffer solution is preferably 30 to 150 mM, more preferably 50 to 120 mM, even more preferably 80 to 120 mM, and for example, 100 mM. The neutral salt at this time is preferably sodium chloride or potassium chloride; however, the salt is particularly preferably sodium chloride.

Elution of the HSA-hGH fusion protein from cation exchange column chromatography is carried out by using a buffer solution having an increased concentration of a neutral salt. The concentration of the neutral salt at this time is preferably 400 to 600 mM, more preferably 500 to 600 mM, even more preferably 530 to 570 mM, and for example, 550 mM.

A fourth column chromatography step is to use size exclusion chromatography. Size exclusion chromatography is intended to remove, in particular, low molecular weight contaminants such as endotoxin, and oligomers and degradation products of the HSA-hGH fusion protein, based on the molecular size.

In the size exclusion chromatography step, the column is equilibrated in advance. Here, the type of the buffer solution is not particularly limited; however, a phosphate buffer solution is preferred, and the concentration thereof is preferably 5 to 20 mM, more preferably 8 to 12 mM, and for example, 10 mM. The pH of the buffer solution is preferably adjusted to 6.6 to 7.4, more preferably to 7.0 to 7.4, and for example, to 7.2. Furthermore, the buffer solution may contain a disaccharide that can be used as a pharmaceutical additive. Such a disaccharide is preferably sucrose, and the concentration thereof is preferably 60 to 90 mg/mL, more preferably 70 to 80 mg/mL, and for example, 75 mg/mL. Through these first to fourth column chromatography steps, substantially pure HSA-hGH fusion protein is obtained.

In the purification step for the HSA-hGH fusion protein, a virus inactivation step may be added as desired. The virus inactivation step may be carried out between any two chromatography steps or may be carried out before the first chromatography step or after the final chromatography step. Furthermore, the virus inactivation step may be carried out once, may be carried out twice, or may be carried out three or more times, during the purification step for the HSA-hGH fusion protein.

When the chromatography steps include a column chromatography step (first column chromatography step) of using a material to which an antibody having an affinity for the HSA-hGH fusion protein is linked, as a stationary phase; a column chromatography step (second column chromatography step) of using a material having an affinity for phosphate group as a stationary phase; a cation exchange column chromatography step (third column chromatography step); and a size exclusion column chromatography step (fourth column chromatography step) in this order, the virus inactivation step is preferably carried out between the first column chromatography step and the second column chromatography step, or/and after the fourth column chromatography step. There is no particular limitation on which virus inactivation step should be applied; however, a solvent-detergent method or a filter filtration method can be suitably applied. The solvent-detergent method is a method of inactivating virus by adding an organic solvent and a surfactant to a solution in which viruses should be inactivated. When the solvent-detergent method is applied, an organic solvent and a nonionic surfactant are added and mixed into a solution containing the HSA-hGH fusion protein, and this mixed liquid is incubated for, for example, more than 3 hours. The solution to be used for the solvent-detergent method is not particularly limited as long as the HSA-hGH fusion protein is stably retained for at least two hours; however, a mixture obtained by mixing an organic solvent and a non-surfactant into a glycine buffer solution, a phosphate buffer solution, an MES buffer solution, a Tris-HCl buffer solution, or a mixture of these, in all of which the pH has been adjusted to near neutrality, can be suitably used. Furthermore, there is also no particular limitation on which nonionic surfactant should be used; however, for example, polysorbate 20, polysorbate 80, and triton X-100 can be used singly or in combination of any of these. Polysorbate 80 is one of particularly suitable nonionic surfactants and can be used singly or in combination with other nonionic surfactants. Furthermore, there is also no particular limitation on which organic solvent should be used; however, for example, tri(n-butyl phosphate) can be used. When polysorbate 80 is used in combination with tri(n-butyl phosphate), the concentration of polysorbate 80 in the mixed liquid is 0.3% to 2%, for example, 1%, the concentration of tri(n-butyl phosphate) is 0.1% to 0.5%, for example, 0.3%, and the mixed liquid is incubated for 2 to 5 hours, for example, for 3 hours.

The filter filtration method is a method of removing viruses by filtering a solution from which viruses should be removed, through a filtration membrane having the performance of removing viruses (virus-removing membrane). The filtration membrane used for the filter filtration method is preferably such that the average pore size is 17 to 21 nm, and the material thereof is, for example, regenerated cellulose. When the filter filtration method is applied, a solution containing the HSA-hGH fusion protein is passed through a virus-removing membrane. For example, virus removal can be more reliably carried out by performing virus inactivation by a solvent-detergent method between the first column chromatography step and the second column chromatography step and performing virus inactivation by a filter filtration method after the fourth column chromatography step.

Incidentally, the method of using a virus-removing membrane can be considered as a virus removal step; however, according to the present invention, the method can also be considered as one method for the virus inactivation step.

According to the present invention, the HSA-hGH fusion protein has increased stability in blood and a prolonged half-life, as compared with the original growth hormone to which HSA is not linked. Although the half-life in blood may vary depending on the route of administration and the dosage, when the HSA-hGH fusion protein is administered to cynomolgus monkeys by subcutaneous injection, the half-life in blood $(t_{1/2}\beta)$ is, for example, 5 hours or longer, and the fusion protein becomes extremely stable in blood. For example, regarding the half-life in blood $(t_{1/2}\beta)$ of the HSA mutant-human growth hormone fusion protein, when the fusion protein is subcutaneously administered once to male cynomolgus monkeys at a dose of 0.5 to 10 mg/kg, the half-life in blood $(t_{1/2}\beta)$ is 5 to 40 hours.

According to the present invention, a medicine containing the HSA mutant-growth hormone fusion protein as an active ingredient can be intravenously, intramuscularly, intraperitoneally, or subcutaneously administered as an injectable preparation.

Human growth hormone mainly has two kinds with different molecular weights, namely, a hormone having a molecular weight of 22 kDa (22 kDa human growth hormone, 22K human growth hormone in the present specification) and a hormone having a molecular weight of 20 kDa (20 kDa human growth hormone, 20K human growth hormone in the present specification). The 22K growth hormone is a protein having an amino acid sequence set forth in SEQ ID NO:9 and composed of 191 amino acids. Usually, when the term "human growth hormone (or hGH)" is said, it means this 22K growth hormone; however, when the term "human growth hormone (or hGH)" is simply said in the present specification, it includes both the 22K human growth hormone and the 20K human growth hormone.

According to the present specification, when the term "22K human growth hormone (or 22KhGH)" is simply said, in addition to the wild-type 22KhGH having an amino acid sequence set forth in SEQ ID NO:9, a 22KhGH mutant in which one amino acid or a plurality of amino acids have been substituted, deleted, and/or added with respect to this wild-type 22KhGH, and which has growth promoting activity, is also included. The number of amino acids that may be substituted, deleted, and/or added is preferably 1 to 8, more preferably 1 to 4, and even more preferably 1 to 2, for each mutation type. Here, the amino acid sequence of the 22KhGH mutant preferably has an identity of 85% or higher, more preferably an identity of 90% or higher, and even more preferably an identity of 95% or higher, with the amino acid sequence of the wild-type 22KhGH set forth in SEQ ID NO:9.

The wild-type 20K human growth hormone corresponds to a protein in which fifteen amino acids from the $32^{nd}$ to the $46^{th}$ positions as counted from the N-terminus among the 191 amino acids constituting the wild-type 22K growth hormone (SEQ ID NO:9) have been deleted, the protein having an amino acid sequence composed of 176 amino acids (SEQ ID NO:10) and having growth promoting activity. However, according to the present specification, when the term "20K human growth hormone (or 20KhGH)" is simply said, in addition to the wild-type 20KhGH set forth in SEQ ID NO:10, a mutant of 20KhGH corresponding to a sequence obtained by substituting, deleting, and/or adding one amino acid or a plurality of amino acids with respect to the sequence of the wild-type 20KhGH, the mutant having growth promoting activity, is also included. The number of amino acids that may be substituted, deleted, and/or added is preferably 1 to 8, more preferably 1 to 4, and even more preferably 1 or 2, for each mutation type. Here, the amino acid sequence of the 20KhGH preferably has an identity of 85% or higher, more preferably an identity of 90% or higher, and even more preferably an identity of 95% or higher, with the amino acid sequence of the wild-type 20KhGH set forth in SEQ ID NO:10.

According to the present invention, the position of each mutation and the form thereof (deletion, substitution, or addition) in each of various hGH mutants as compared with normal wild-type hGH can be easily checked by checking the alignment of the amino acid sequences of the two hGHs. According to the present invention, the identity between the amino acid sequence of wild-type hGH and the amino acid sequence of hGH to which mutation has been applied, can be easily calculated by using well-known homology calculation algorithms. Examples of such algorithms include BLAST (Altschul S F, J Mol. Biol., 215, 403-10 (1990)), the similarity search method of Pearson and Lipman (Proc. Natl. Acad. Sci., USA, 85, 2444 (1988)), and the local homology algorithm of Smith and Waterman (Adv. Appl. Math., 2, 482-9 (1981)).

The substitution of an amino acid in the above-described amino acid sequence of hGH with another amino acid occurs, for example, within a family of amino acids that are relevant in terms of the side chains and chemical characteristics of those amino acids. Such substitution within a family of amino acids is not expected to bring significant changes in the functions of hGH (that is, conservative amino acid substitution). Examples of such a family of amino acids include the following:

(1) aspartic acid and glutamic acid, which are acidic amino acids, (2) histidine, lysine, and arginine, which are basic amino acids, (3) phenylalanine, tyrosine, and tryptophan, which are aromatic amine acids, (4) serine and threonine, which are amino acids having a hydroxy group (hydroxyamino acids), (5) methionine, alanine, valine, leucine, and isoleucine, which are hydrophobic amino acids, (6) cysteine, serine, threonine, asparagine, and glutamine, which are neutral hydrophilic amino acids, (7) glycine and proline, which are amino acids affecting the alignment of peptide chains, (8) asparagine and glutamine, which are amide type amino acids (polar amino acids), (9) alanine, leucine, isoleucine, and valine, which are aliphatic amino acids,

(10) alanine, glycine, serine, and threonine, which are amino acids having a small side chain, and

(11) alanine and glycine, which are amino acids having a particularly small side chain.

Preparations containing, as an active ingredient, a hGH (hGH preparations) having a molecular weight of about 22 kD produced as a recombinant protein by using hGH gene-introduced *Escherichia coli* have been clinically widely used as therapeutic agents for growth hormone deficiency dwarfism, short stature associated with Turner syndrome, Small-for-Gestational Age (SGA) dwarfism, dwarfism associated with Noonan syndrome, dwarfism caused by chronic renal failure, dwarfism associated with Prader-Willi syndrome, and dwarfism associated with cartilage dystrophy. hGH preparations are particularly effective in a case where these diseases are not accompanied by epiphyseal closure. When hGH preparations are administered subcutaneously or intramuscularly, hGH circulates in the blood and exhibits an effect of promoting the growth of a patient by the growth promoting activity of hGH. Furthermore, hGH preparations are widely clinically used as a therapeutic agent for adult growth hormone deficiency. In patients with adult growth hormone deficiency, abnormal lipid metabolism is observed; however, when an hGH preparation is administered, the patient's lipid metabolism is normalized, and the QOL of the patient is improved. Growth hormone is clinically applied also as a therapeutic agent for exhaustion caused by AIDS. As an hGH preparation for growth hormone deficiency dwarfism, adult growth hormone deficiency, and the like, for example, GROWJECT (registered trademark) is available.

When a fusion protein of an HSA mutant and hGH is produced, regarding a specific method of linking a polypeptide including the amino acid sequence of the HSA mutant and a polypeptide including the amino acid sequence of hGH, for example, a method of producing an expression vector having a DNA fragment incorporated therein, the DNA fragment being a DNA fragment in which a gene encoding one of the polypeptides is linked in-frame downstream of a gene encoding the other polypeptide, and culturing host cells that have been transformed by using this expression vector to express the fusion protein as a recombinant protein, is general and can be utilized for the present invention.

When a fusion protein of an HSA mutant and hGH is produced by a method of expressing the fusion protein in transformed cells as a recombinant protein, a polypeptide including the amino acid sequence of hGH is linked to either the N-terminal side or the C-terminal side of a polypeptide including the amino acid sequence of the HSA mutant directly or indirectly through a linker.

When the polypeptide including the amino acid sequence of hGH is linked to the N-terminal side of the polypeptide including the amino acid sequence of the HSA mutant, an expression vector having a DNA fragment incorporated therein, the DNA fragment being a DNA fragment in which a gene encoding the polypeptide that includes the amino acid sequence of the HSA mutant is linked in-frame downstream of a gene encoding the polypeptide that includes the amino acid sequence of hGH, is used. When the two polypeptides are indirectly linked through a peptide linker, a DNA sequence encoding the linker is disposed in-frame between the genes encoding the two polypeptides.

When the polypeptide including the amino acid sequence of hGH is linked to the C-terminal side of the polypeptide including the amino acid sequence of the HSA mutant, an expression vector having a DNA fragment incorporated therein, the DNA fragment being a DNA fragment in which a gene encoding the polypeptide that includes the amino acid sequence of the HSA mutant is linked in-frame upstream of a gene encoding the polypeptide that includes the amino acid sequence of hGH, is used. When the two polypeptides are indirectly linked via a peptide linker, a DNA sequence encoding the linker is disposed in-frame between the genes encoding the two polypeptides.

According to the present invention, as a suitable example of the fusion protein of an HSA mutant and hGH (one kind of HSA-hGH fusion proteins), an HSA-hGH fusion protein having an amino acid sequence set forth in SEQ ID NO:11, in which the C-terminus of 22K human growth hormone having the amino acid sequence set forth in SEQ ID NO:9 is linked to the N-terminus of HSA (A320T) having the amino acid sequence set forth in SEQ ID NO:3 by peptide bonding, with a linker interposed therebetween, may be mentioned. According to the present invention, a product obtained by linking HSA (A320T) and 22KhGH in this order is referred to as "22K human growth hormone-mHSA" or "22KhGH-mHSA". Similarly, a product in which the N-terminus of 22K human growth hormone is linked to the C-terminus of HSA (A320T) by peptide bonding, with a linker interposed therebetween, is referred to as "mHSA-22K human growth hormone" or "mHSA-22KhGH".

Furthermore, an HSA-hGH fusion protein having an amino acid sequence set forth in SEQ ID NO:12, in which the C-terminus of 20K human growth hormone having the amino acid sequence set forth in SEQ ID NO:1 is linked to the N-terminus of human serum albumin (A320T) having the amino acid sequence set forth in SEQ ID NO:3 by peptide bonding, with a linker interposed therebetween, is referred to as "20K human growth hormone-mHSA" or "20KhGH-mHSA". Similarly, a product in which the N-terminus of 20K human growth hormone is linked to the C-terminus of human serum albumin (A320T) by peptide bonding, with a linker interposed therebetween, is referred to as "mHSA-20K human growth hormone" or "mHSA-20KhGH".

According to the present invention, the HSA-hGH fusion protein has a feature that when the HSA-hGH fusion protein is administered to cynomolgus monkeys by subcutaneous injection, the half-life in blood $(t_{1/2}\beta)$ is approximately 5 hours or longer, and the fusion protein becomes extremely stable in blood. Although the half-life in blood may vary depending on the dosage, for example, when the fusion proteins are subcutaneously administered once to male cynomolgus monkeys at a dose of 4 mg/kg, the half-life in blood $(t_{1/2}\beta)$ of mHSA-22KhGH and 22KhGH-mHSA is 20 to 35 hours.

The HSA-hGH fusion protein according to the present invention can be used as a medicine. The HSA-hGH fusion protein can coordinate the functions of human growth hormone and HSA in vivo.

The HSA-hGH fusion protein according to the present invention is extremely stable in blood. Therefore, according to the present invention, human growth hormone can be stabilized in blood to stay in blood in a state of retaining activity over a long period of time. Therefore, when this fusion protein is used as a medicine, the frequency of administration or/and the dosage can be reduced as compared to human growth hormone. For example, human growth hormone needs to be administered daily; however, with this fusion protein, the frequency of administration can be adjusted to, for example, every 3 to 30 days. Furthermore, it is also possible to reduce the total dosage of the medicine during the treatment period to, for example, 1/3 or less (for example, 1/3 to 1/10) in terms of molar ratio.

The HSA-hGH fusion protein according to the present invention can be used as a medicine for growth hormone deficiency dwarfism, short stature associated with Turner syndrome, dwarfism caused by chronic renal failure, dwarfism associated with Prader-Willi syndrome, and dwarfism associated with cartilage dystrophy, SGA dwarfism, and dwarfism associated with Noonan syndrome, as target diseases. hGH preparations are particularly effective in a case where these diseases are not accompanied by epiphyseal closure. In addition to that, the HSA-hGH fusion protein according to the present invention can be used as a medicine for adult growth hormone deficiency, exhaustion caused by AIDS, and exhaustion caused by anorexia, as target diseases; however, these diseases are not limited to these, the HSA-hGH fusion protein can be used as a therapeutic agent for diseases in which symptoms can be improved by causing growth promoting activity such as cartilage formation promotion and protein assimilation promotion, and physiological activity such as body composition and lipid metabolism improving action, to be effected for a long time period.

There is no particular limitation on the dosage regimen at the time of administering 22KhGH-mHSA to a human for therapeutic purposes, as long as the efficacy of hGH is exhibited. The dosage regimen of 22KhGH-mHSA will be described with examples below; however, the dosage regime is not limited to these.

When 22KhGH-mHSA is administered to a patient with growth hormone deficiency dwarfism that is not accompanied by epiphyseal closure, a preferred dosage per dose is 0.01 to 0.7 mg/Kg of body weight. When 22KhGH-mHSA is administered to a patient with dwarfism associated with Turner syndrome that is not accompanied by epiphyseal closure, a preferred dosage per dose is 0.015 to 1.4 mg/Kg of body weight. When 22KhGH-mHSA is administered to a patient with dwarfism caused by chronic renal failure that is not accompanied by epiphyseal closure, a preferred dosage per dose is 0.01 to 1.4 mg/Kg of body weight. When 22KhGH-mHSA is administered to a patient with dwarfism associated with Prader-Willi syndrome that is not accompanied by epiphyseal closure, a preferred dosage per dose is 0.012 to 0.98 mg/Kg of body weight. When 22KhGH-mHSA is administered to a patient with dwarfism associated with cartilage dystrophy that is not accompanied by epiphyseal closure, a preferred dosage per dose is 0.015 to 1.4 mg/Kg of body weight. When 22KhGH-mHSA is administered to a patient with SGA dwarfism that is not accompanied by epiphyseal closure, a preferred dosage per dose is 0.012 to 1.9 mg/Kg of body weight. When 22KhGH-mHSA is administered to a patient with adult growth hormone deficiency, a preferred dosage per dose is 0.001 to 0.34 mg/Kg of body weight. When 22KhGH-mHSA is administered to a patient with dwarfism associated with Noonan syndrome that is not accompanied by epiphyseal closure, a preferred dosage per dose is 0.013 to 1.8 mg/Kg of body weight. When 22KhGH-mHSA is administered to a patient exhaustion by AIDS, a preferred dosage per dose is 0.005 to 0.4 mg/Kg of body weight. However, the dosage should be appropriately changed depending on the patient's laboratory findings and the like. Furthermore, a preferred administration interval of 22KhGH-mHSA for these diseases is once every 7 to 30 days, and the administration interval should be appropriately changed to once every 7 to 14 days, every 10 to 20 days, or every 14 to 21 days, depending on the patient's laboratory findings and the like. Furthermore, the method of administration is preferably subcutaneous injection, intramuscular injection, or intravenous injection, and more preferably subcutaneous injection or intramuscular injection.

The aqueous pharmaceutical composition according to the present invention contains a protein obtained by linking serum albumin and growth hormone, as an active ingredient, an antiseptic agent, sucrose, and a nonionic surfactant mainly as stabilizers, and a buffering agent as a pH adjusting agent.

The concentration of the protein obtained by linking serum albumin and growth hormone (particularly 22KhGH-mHSA) to be included in the aqueous pharmaceutical composition is preferably 10 to 100 mg/mL, more preferably 15 to 70 mg/mL, even more preferably 30 to 65 mg/mL, still more preferably 40 to 60 mg/mL, and for example, 50 mg/mL.

The antiseptic agent to be contained in the aqueous pharmaceutical composition is not particularly limited as long as the antiseptic agent is pharmaceutically acceptable; however, phenol is preferred. When phenol is used as an antiseptic agent, the concentration of phenol to be contained in the aqueous pharmaceutical composition is preferably 0.5 to 12 mg/mL, more preferably 3 to 9 mg/mL, even more preferably 4 to 8 mg/mL, still more preferably 5 to 7 mg/mL, and for example, 6 mg/mL.

The concentration of sucrose to be contained in the aqueous pharmaceutical composition is preferably 10 to 150 mg/mL, more preferably 50 to 100 mg/mL, even more preferably 60 to 90 mg/mL, still more preferably 70 to 80 mg/mL, and for example, 75 mg/mL.

Regarding the nonionic surfactant to be contained in the aqueous pharmaceutical composition, polysorbate, poloxamer, and the like can be used singly or in combination of these. As the polysorbate, polysorbate 20 and polysorbate 80 are particularly suitable, and as the poloxamer, poloxamer 188 (polyoxyethylene (160) polyoxypropylene (30) glycol) is particularly suitable. Furthermore, the concentration of the nonionic surfactant to be contained in the aqueous pharmaceutical composition is preferably 0.15 to 10 mg/mL, more preferably 1.0 to 4.5 mg/mL, even more preferably 1.5 to 4.5 mg/mL, still more preferably 2 to 4 mg/mL, even more preferably 2.5 to 3.5 mg/mL, and for example, 3 mg/mL.

The buffering agent to be contained in the aqueous pharmaceutical composition is not particularly limited as long as the buffering agent is pharmaceutically acceptable; however, a phosphate buffering agent is preferred. When a phosphate buffering agent is used as the buffering agent, the concentration of the phosphate buffering agent to be contained in the aqueous pharmaceutical composition is preferably 1 to 30 mM, more preferably 2 to 20 mM, even more preferably 5 to 15 mM, and for example, about 10 mM. Furthermore, the pH of the aqueous pharmaceutical composition to be adjusted by the buffering agent is preferably 5.0 to 8.0, more preferably 6.0 to 7.8, even more preferably 6.5 to 7.6, still more preferably 7.0 to 7.4, and for example, 7.2. The osmotic pressure ratio of the aqueous pharmaceutical composition with respect to physiological saline is adjusted to, for example, 1.0 to 1.3.

Regarding a suitable composition of the aqueous pharmaceutical composition of the present invention, a composition in which the concentration of the protein obtained by linking serum albumin and growth hormone (particularly 22KhGH-mHSA) is 10 to 100 mg/mL, the concentration of the antiseptic agent is 0.5 to 12 mg/mL, the concentration of sucrose is 10 to 150 mg/mL, the concentration of the nonionic surfactant is 0.15 to 10 ng/mL, the concentration of the antiseptic agent is 0.5 to 12 mg/mL, the concentration of the buffering agent is 1 to 30 mM, and the pH is 5.0 to 8.0, may be mentioned.

Furthermore, regarding a suitable composition of the aqueous pharmaceutical composition of the present invention, a composition in which the concentration of the protein obtained by linking serum albumin and growth hormone (particularly 22KhGH-mHSA) is 10 to 100 mg/mL, the concentration of sucrose is 75 mg/mL, the concentration of polyoxyethylene (160) polyoxypropylene (30) glycol is 3 mg/mL, the concentration of phenol is 6 mg/mL, the concentration of the phosphate buffering agent is 10 mM, and the pH is 7.0 to 7.4, may be mentioned. The concentration of each component can be changed to any of the above-described preferred concentrations.

In addition, regarding a suitable composition of the aqueous pharmaceutical composition of the present invention, a composition in which the concentration of the protein obtained by linking serum albumin and growth hormone (particularly 22KhGH-mHSA) is 15 to 70 mg/mL, the concentration of sucrose is 75 mg/mL, the concentration of polyoxyethylene (160) polyoxypropylene (30) glycol is 3 mg/mL, the concentration of phenol is 6 mg/mL, the concentration of the phosphate buffering agent is 10 mM, and the pH is 7.0 to 7.4, may be mentioned. The concentration of each component can be changed to any of the above-described preferred concentrations.

A medicine containing the HSA-hGH fusion protein (particularly 22KhGH-mHSA) of the present invention as an active ingredient can be administered intravenously, intramuscularly, intraperitoneally, subcutaneously, or intraventricularly as an injectable preparation. Those injectable preparations can be supplied as freeze-dried preparations or aqueous liquid preparations (aqueous pharmaceutical compositions). When the medicine is prepared into an aqueous liquid preparation, the aqueous liquid preparation may be in the form of being filled in a vial or may be supplied as a prefilled-type preparation, which has been filled in advance in a syringe. In the case of a lyophilized preparation, the preparation is dissolved in an aqueous medium to be restored before use and then used.

EXAMPLES

Hereinafter, the present invention will be described in more detail with reference to Examples; however, the present invention is not intended to be limited to the Examples.

[Example 1] Construction of Vector for 22KhGH-HSA Expression

A protein having an amino acid sequence set forth in SEQ ID NO:15, in which the C-terminus of 22KhGH is linked to the N-terminal of wild-type HSA (SEQ ID NO:1), was designated as 22KhGH-HSA. In the amino acid sequence set forth in SEQ ID NO:15, the $1^{st}$ to $191^{st}$ amino acid residues correspond to the amino acid sequence of 22KhGH, and the $192^{nd}$ to $776^{th}$ amino acid residues correspond to the amino acid sequence of HSA. A DNA having a base sequence set forth in SEQ ID NO:16, which included a gene encoding 22KhGH-HSA (22KhGH-HSA gene), was chemically synthesized. With regard to this sequence, bases 11 to 88 encode a leader peptide of hGH, bases 89 to 661 encode mature type hGH, and bases 662 to 2416 encode mature type HSA. This DNA was digested with restriction enzymes (MluI and NotI) and was incorporated between the MluI site and the NotI site of pE-mIRES-GS-puro, and thereby pE-mIRES-GS-puro (22KhGH-HSA), which is a vector for 22KhGH-HSA expression, was constructed. Incidentally, regarding pE-mIRES-GS-puro, the production method is described in WO 2012/063799 and the like and is well known.

[Example 2] Construction of Vector for 22KhGH-mHSA Expression

A protein having an amino acid sequence set forth in SEQ ID NO:11, in which the C-terminus of 22KhGH (SEQ ID NO:9) was linked to the N-terminus of HSA (A320T) (SEQ ID NO:3), was designated as 22KhGH-mHSA. A DNA fragment including a gene encoding 22KhGH-mHSA was amplified by PCR by using the pE-mIRES-GS-puro (22KhGH-HSA) produced in Example 1 as a template and using primer YA082 (SEQ ID NO:13) and primer YA083 (SEQ ID NO:14). This DNA fragment was self-annealed to construct pE-mIRES-GS-puro (22KhGH-mHSA), which was a vector for 22KhGh-mHSA expression.

[Example 3] Production of 22KhGH-mHSA Expressing Cell Line

Cells for expressing 22KhGH-mHSA were produced as follows. pE-mIRES-GS-puro (22KhGH-mHSA), which was a vector for 22KhGH-mHSA expression, produced in Example 2 was introduced into CHO-K1 cells, which are cells derived from the ovary of a Chinese hamster, by using a Gene Pulser Xcell electroporation system (Bio-Rad Laboratories, Inc.). Cells having the expression vector introduced therein were selectively cultured by using CD OPTICHO™ medium (Thermo Fisher Scientific, Inc.) including 16 μM thymidine, 100 μM hypoxanthine, 10 mg/L insulin, L-methionine sulfoximine (Sigma-Aldrich Corp.), and puromycin (Sigma-Aldrich Corp.). During the selective culture, the concentrations of L-methionine sulfoximine and puromycin were increased stepwise to finally set the concentration of L-methionine sulfoximine to 300 M and the concentration of puromycin to 10 g/mL, and cells exhibiting higher drug resistance were selectively proliferated. Next, the cells selected by selective culture were seeded onto a 96-well plate such that not more than one cell was seeded per well by a limiting dilution method, the cells were cultured for about 10 days until single cell-derived colonies were formed to clone the cells. The cloned cells were further cultured to proliferate and then were suspended in CD OPTICHO™ medium containing 16 M thymidine, 100 M hypoxanthine, 300 M L-methionine sulfoximine, and 10% (v/v) DMSO, and subsequently the cells were dispensed in cryotubes and stored in liquid nitrogen. These cells were designated as 22KhGH-mHSA expressing cell line.

[Example 4] Preculture of 22KhGH-mHSA Expressing Cells

The 22KhGH-mHSA expressing cell line produced in Example 3 was dissolved in a water bath at 37° C., suspended in EX-CELL® Advanced medium (medium for preculture, Sigma-Aldrich Corp.) of a serum-free medium including 16 M thymidine, 100 M hypoxanthine, and 300 M L-methionine sulfoximine, and centrifuged to precipitate the cells, and the supernatant was removed. The precipitated cells were suspended in the medium for preculture at a density of $2 \times 10^5$ cells/mL or more, and the cells were cultured for 2 to 4 days at 37° C. in the presence of 5% $CO_2$. This culture was repeated while expanding the culture scale until the number of cells increased to at least $1.0 \times 10^{11}$ cells.

[Example 5] Production Culture of 22KhGH-mHSA Expressing Cells

The cells proliferated in preculture were suspended in EX-CELL® Advanced medium (medium for production culture, Sigma-Aldrich Corp.), which was a serum-free medium including 16 μM thymidine and 100 μM hypoxanthine, in a volume of 200 L at a cell concentration of a density of $4 \times 10^5$ cells/mL. This suspension was cultured in a single-use culture tank of an XCELLEREX™ 200L culture system (XDR200) for 10 days while being stirred with an impeller at a rate of 100 rpm, with the culture system maintained at 37° C., a dissolved oxygen content of 40%, and a pH of 6.9.

[Example 6] Purification of 22KhGH-mHSA (Purification Step 1: Harvest Step/Concentration 1 Step)

After completion of the production culture, the culture fluid was filtered by using MILLISTAK+® (registered trademark) HC Pod Filter Grade DOHC (1.1 $m^2 \times 2$, Merck KGaA) and then was filtered by using MILLISTAK+® HC Pod Filter Grade X0HC (1.1 $m^2 \times 1$, Merck KGaA) to remove cells, and the resultant was further filtered through OPTI-CAP® SHC XL3 (pore size: 0.5/0.2 μm, Merck KGaA) to obtain a culture supernatant. The obtained culture supernatant was washed in advance with pure water and then was concentrated by using an ultrafiltration membrane device (equipped with PELLICON® 3 Cassette ULTRACEL® PLCTK membrane, 1.14 $m^2$, Merck KGaA) equilibrated with PBS and having a molecular weight cutoff of 30 kDa. The solution after concentration was collected from the ultrafiltration membrane device. Furthermore, the inside of the device was washed by passing PBS therethrough, this washing liquid was combined with the solution after concentration that had been collected first, subsequently the weight was adjusted to about 15 kg, and this was used as concentrated culture fluid. Next, the concentrated culture fluid was filtered by using a hydrophilic filter (OPTICAP® SHC XL600, Merck KGaA) having a maximum pore size of 0.5 μm and a minimum pore size of 0.2 μm. After the filtration, it was confirmed that the pH and conductivity of the concentrated culture fluid were 7.0±0.3 and 1.2±0.4 S/m, respectively.

(Purification Step 2: First Chromatography Step (Affinity Column Chromatography Step))

A QS column (column volume: 4.2 to 5.2 L, bed height: 15.0±1.5 cm, Merck KGaA) packed with Capture select Human Growth Hormone Affinity Matrix (Thermo Fisher Scientific, Inc.) was washed with a 50 mM glycine hydrochloric acid buffer solution (pH 3.0) in a volume 1 times the volume of the column and a 0.01 M aqueous solution of sodium hydroxide in a volume 1 times the volume of the column and then was equilibrated with a 20 mM Tris-HCl buffer solution (pH 7.0) in a volume 4 times the volume of the column. Next, a 1/4 amount of the concentrated culture fluid obtained in purification step 1 was loaded on the column, and 22KhGH-mHSA was adsorbed to the column. Next, the column was washed with a 20 mM Tris-HCl buffer solution (pH 7.0) containing 200 mM arginine and 0.05% (w/v) polysorbate 80 in a volume 5 times the volume of the column, and a 20 mM Tris-HCl buffer solution (pH 7.0) in a volume 5 times the volume of the column. Next, a 50 mM glycine hydrochloric acid buffer solution (pH 3.0) in a volume 5 times the volume of the column was supplied to the column, and 22KhGH-mHSA was eluted. The eluate was collected in a container containing a 250 mM MES buffer solution (pH 7.0) in a capacity of ⅕ the amount of the eluate in advance and was immediately neutralized such that the pH became 6.7±0.3. Purification step 2 was carried out at a cold temperature of 4° C. to 8° C., and the linear flow rate of the solution to be supplied to the column was set to 200 cm/hour throughout the purification step 2. Furthermore, the upper limit of 22KhGH-mHSA to be loaded per 1 L of the affinity column carrier was set to 7 g.

(Purification Step 3: Virus Inactivation Step)

The eluate obtained in purification step 2 was warmed to 25° C., a 6.01 (v/v) aqueous solution of tri(n-butyl) phosphate containing 20.0% (w/v) polysorbate 80 in a capacity of 1/19 the liquid amount of the eluate was added to the eluate, and the mixture was stirred at 25° C. for 3 hours.

(Purification Step 4: Second Chromatography Step (Hydroxyapatite Column Chromatography Step))

The fraction that had been subjected to a virus inactivation treatment in purification step 3 was cooled to 8° C., an appropriate amount of a 20 mM MES buffer solution (pH 7.0) containing a 1 M Tris-HCl buffer solution (pH 8.8) and 4 M NaCl was added thereto to adjust the pH and the conductivity to 7.0±0.1 and 0.6±0.1 S/m, respectively, and the resultant was filtered by using a hydrophilic filter (Merck KGaA) having a pore size of 0.2 μm. Next, the following chromatography was carried out under refrigeration (linear flow rate: 200 cm/hour).

A QS column (column volume: 8.8 to 10.8 L, bed height: 20.0±2.0 cm, Merck KGaA) packed with CHT Type II, 40 μm (Bio-Rad Laboratories, Inc.), which was a hydroxyapatite carrier, was washed with a 200 mM phosphate buffer solution (pH 7.0), subsequently a 1 M aqueous solution of NaOH, and a 200 mM phosphate buffer solution (pH 7.0), and then the column was equilibrated with a 20 mM MES Buffer solution (pH 7.0) containing 50 mM NaCl and 1 mM sodium dihydrogen phosphate in a volume 4 times the volume of the column. Next, the above-described liquid was loaded on the column, and 22KhGH-mHSA was adsorbed to the column. Next, the column was washed with a 20 mM MES buffer solution (pH 7.0) containing 50 mM NaCl and 1 mM sodium dihydrogen phosphate in a volume 3 times the volume of the column. Next, a 20 mM MES buffer solution (pH 7.0) containing 50 mM NaCl and 30 mM sodium dihydrogen phosphate was supplied to the column to elute 22KhGH-mHSA. Purification step 4 was carried out at a cold temperature of 4° C. to 8° C., and the linear flow rate of the solution supplied to the column was set to 200 cm/hour throughout the purification step 4. Furthermore, the upper limit of 22KhGH-mHSA to be loaded per 1 L of the hydroxyapatite carrier was set to 13 g.

(Purification Step 5: Third Chromatography Step (Multimodal Weak Cation Exchange Column Chromatography Step))

To the eluate obtained in purification step 4, a 20 mM MES buffer solution (pH 5.7) containing 50 mM NaCl in the same volume as the volume of this eluate was added, subsequently dilute hydrochloric acid was added thereto to adjust the pH and the conductivity to 5.7±0.1 and 0.7±0.1 S/m, respectively. Subsequently, the mixture was filtered by using a hydrophilic filter (Merck KGaA) having a pore size of 0.5/0.2 μm.

A prepacked column RTP Capto MMC 10L (column volume: 8.8 to 10.8 L, bed height: 20.0±2.0 cm, Merck KGaA) was washed by using a 1 M aqueous solution of NaOH and then a 50 mM phosphate buffer solution (pH 7.0) containing 1 M NaCl and then was equilibrated with a 50 mM MES buffer solution (pH 5.7) containing 100 mM NaCl in a volume 4 times the volume of the column. Next, the above-described liquid was loaded on the column, and 22KhGH-mHSA was adsorbed to the column. Next, the column was washed with a 50 mM MES buffer solution (pH 5.7) containing 100 mM NaCl in a volume 5 times the volume of the column. Next, a 50 mM MES buffer solution (pH 5.7) containing 550 mM NaCl was supplied to the column to elute 22KhGH-mHSA. Purification step 5 was carried out at a cold temperature of 4° C. to 8° C., and the linear flow rate of the solution to be supplied to the column was set to 200 cm/hour throughout the purification step 5. Furthermore, the upper limit of 22KhGH-mHSA to be loaded per 1 L of the multimodal weak cation exchange carrier was set to 11.5 g.

(Purification Step 6: Concentration 2 Step)

Pure water was passed through an ultrafiltration membrane (PELLICON® 3 Cassette ULTRACEL® PLCTK membrane 1.14 m², Merck KGaA) having a molecular weight cutoff of 30 kDa to sufficiently wash the membrane, and then the ultrafiltration membrane was equilibrated with a 10 mM phosphate buffer solution (pH 7.2) containing 75 mg/mL sucrose. The eluate obtained in purification step 5 was concentrated by using this ultrafiltration membrane. To the solution after concentration, a 10 mM phosphate buffer solution (pH 7.2) containing 75 mg/mL sucrose was added to adjust the light absorbance (280 nm) to 23±3. This concentration step was carried out at room temperature.

(Purification Step: Fourth Chromatography Step (Size Exclusion Column Chromatography Step))

The concentrated liquid obtained in purification step 6 was filtered by using a hydrophilic filter (Merck KGaA) having a pore size of 0.5/0.2 μm. A QS column (column volume: 25.4 to 31.1 L, bed height: 40.0±4.0 cm, Merck KGaA) packed with FRACTOGEL® BioSEC resin (synthetic methacrylate-based chromatography resin, Merck KGaA), which is a resin for size exclusion chromatography, was washed with a 0.5 M aqueous solution of NaOH, and then the column was equilibrated with a 10 mM phosphate buffer solution (pH 7.2) containing 75 mg/mL sucrose. Next, the above-described liquid was loaded on the column, and subsequently a 10 mM phosphate buffer solution (pH 7.2) containing 75 mg/mL sucrose was supplied thereto. At this time, an absorptiometer for continuously measuring the absorbance of the eluate was disposed in the flow channel of the eluate from the size exclusion column, the absorbance at 280 nm was monitored, a fraction showing an absorption peak at 280 nm was collected as the fraction including 22KhGH-mHSA, and this was used as a 22KhGH-mHSA purified product. Purification step 7 was carried out at room temperature, and the linear flow rate of the solution to be supplied to the column was set to 30 cm/hour or less throughout the purification step 7. Furthermore, the liquid amount of the filtrate containing 22KhGH-mHSA to be loaded on the multimodal weak cation exchange carrier was set to be 8% or less of the volume of the carrier.

(Purification Step 8: Concentration 3 Step)

A hollow fiber membrane (ReadyToProcess Hollow Fiber Cartridge, molecular weight cutoff 30 kDa, GE Healthcare Systems) was equilibrated with a 10 mM phosphate buffer solution (pH 7.2) containing 75 mg/mL sucrose. The 22KhGH-mHSA purified product obtained in purification step 7 was concentrated by using this hollow fiber membrane, and the concentration of 22KhGH-mHSA was adjusted to 85 mg/mL. To the obtained concentrated liquid, a 10 mM phosphate buffer solution (pH 7.2) containing 90 mg/mL Poloxamer 188 and 75 mg/mL sucrose in a capacity of $\frac{1}{29}$ of the liquid amount of the concentrated liquid was added and mixed, and the mixture was filtered by using a hydrophilic filter (Merck KGaA) having a pore size of 0.5/0.2 μm. This concentration step was carried out at room temperature.

(Purification Step 9: Virus Removal Step)

A 10 mM phosphate buffer solution (pH 7.2) containing 3 mg/mL Poloxamer 188 and 75 mg/mL sucrose was produced. A virus removal membrane (Planova 20 N, membrane area: 0.12 m², material: regenerated cellulose, Asahi Kasei Medical Co., Ltd.) was equilibrated by using this buffer solution. The filtrate obtained in purification step 8 was passed through this virus removal membrane at a pressure of 98 kPa or less to be filtered. This virus removal step was carried out at room temperature.

(Purification Step 10: Drug Substance Conversion Step)

The filtrate obtained in purification step 9 was filtered at room temperature through a hydrophilic filter (Merck KGaA) having a pore size of 0.2 μm, and 22KhGH-mHSA drug substance was obtained.

[Example 7] Examination 1 of Stability of Aqueous Pharmaceutical Composition Containing 22KhGH-mHSA Six kinds of aqueous pharmaceutical compositions (formulations 1-1 to 1-6) containing 15 mg/mL 22KhGH-mHSA and a 20 mM phosphate buffering agent and having the compositions indicated in Table 1, with different pH values, were prepared by using the 22KhGH-mHSA drug substance obtained in Example 6.

product thereof, included in each of the solutions were measured by the SE-HPLC analysis described in Example 13. The results are presented in Table 2. Here, it was defined in advance as the condition for a stable aqueous pharmaceutical composition that the ratio of the polymer and low molecular weight species included in the solutions after standing for one week at 5° C. and for one week at 40° C. in a dark place was approximately 2% or less in all cases. The results of Table 2 show that under these measurement conditions, in order to obtain a stable aqueous pharmaceutical composition of 22KhGH-mHSA, it is preferable to set the pH to be 6.0 or higher, and it is particularly preferable to set the pH to 6.5 to 7.5.

TABLE 2

Results of SE-HPLC analysis for aqueous pharmaceutical compositions (formulations 1-1 to 1-6)

| | | Ratio (%) | | |
| | | Mono-mer | Poly-mer | Low molecular weight species |
| Sample | Measurement point | | | |
|---|---|---|---|---|
| Formulation 1-1 (pH 5.0) | Immediately after preparation | 97.19 | 2.80 | 0.01 |
| | 5° C. 1 W | 97.77 | 2.21 | 0.02 |
| | 40° C. 1 W | 91.93 | 6.92 | 1.16 |
| Formulation 1-2 (pH 5.5) | Immediately after preparation | 97.66 | 2.33 | 0.01 |
| | 5° C. 1 W | 97.83 | 2.15 | 0.01 |
| | 40° C. 1 W | 96.67 | 2.83 | 0.50 |
| Formulation 1-3 (pH 6.0) | Immediately after preparation | 98.15 | 1.84 | 0.01 |
| | 5° C. 1 W | 98.10 | 1.89 | 0.01 |
| | 40° C. 1 W | 97.48 | 2.01 | 0.51 |
| Formulation 1-4 (pH 6.5) | Immediately after preparation | 98.35 | 1.64 | 0.01 |
| | 5° C. 1 W | 98.34 | 1.65 | 0.01 |
| | 40° C. 1 W | 97.88 | 1.63 | 0.49 |
| Formulation 1-5 (pH 7.0) | Immediately after preparation | 98.32 | 1.67 | 0.01 |
| | 5° C. 1 W | 98.33 | 1.66 | 0.01 |
| | 40° C. 1 W | 98.09 | 1.48 | 0.44 |
| Formulation 1-6 (pH 7.6) | Immediately after preparation | 98.37 | 1.62 | 0.01 |
| | 5° C. 1 W | 98.36 | 1.63 | 0.01 |
| | 40° C. 1 W | 98.12 | 1.48 | 0.40 |

[Example 8] Examination 2 of Stability of Aqueous Pharmaceutical Composition Containing 22KhGH-mHSA Three kinds of aqueous pharmaceutical compositions (formulations 2-1 to 2-3) containing 15 mg/mL 22KhGH-

TABLE 1

Composition of aqueous pharmaceutical compositions (formulations 1-1 to 1-6)

| Ingredients | Formulation 1-1 | Formulation 1-2 | Formulation 1-3 | Formulation 1-4 | Formulation 1-5 | Formulation 1-6 |
|---|---|---|---|---|---|---|
| 22KhGH-mHSA | | | | 15 mg/mL | | |
| Phosphate buffering agent | | | | 20 mM | | |
| Hydrochloric acid or sodium hydroxide | necessary amount | necessary amount | necessary amount | necessary amount | necessary amount | necessary amount |
| pH | 5.0 | 5.5 | 6.0 | 6.5 | 3.0 | 7.5 |

60

1.5 mL each of the six kinds of aqueous pharmaceutical compositions were each filled in a glass vial, and the vials were left to stand and stored in a dark place for one week at 5° C. or for one week at 40° C. After the standing, the ratio of a monomer of 22KhGH-mHSA, a polymer thereof, and low molecular weight species, which was a degradation mHSA and a 20 mM phosphate buffering agent and having the compositions indicated in Table 3, with different concentrations of sucrose and sodium chloride, were prepared by using the 22KhGH-mHSA drug substance obtained in Example 6. For all the solutions, the pH was adjusted to 7.0, and the osmotic pressure ratio was adjusted to about 1.0.

Using a protein property analyzer (Optim1000, AVACTA Group plc), 9 μL of a measurement sample was introduced into a cuvette (UNi, UNCHAINED LABS, Inc.), the cuvette was heated from 20.0° C. to 96.0° C. at an increment of 1° C., and the static light scattering intensity at a wavelength of 473 nm was measured at each temperature.

TABLE 3

| Composition of aqueous pharmaceutical compositions (formulations 2-1 to 2-3) | | | |
|---|---|---|---|
| Ingredients | Formulation 2-1 | Formulation 2-2 | Formulation 2-3 |
| 22KhGH-mHSA | | 15 mg/mL | |
| Phosphate buffering agent | | 20 mM | |
| Sucrose | 70 mg/mL | 53 mg/mL | 33 mg/mL |
| Sodium chloride | 0 mM | 25 mM | 55 mM |
| Hydrochloric acid or sodium hydroxide | necessary amount | necessary amount | necessary amount |
| pH | | 7.0 | |

A graph of the results of measuring the static light scattering intensity is shown in FIG. 1. In FIG. 1, the axis of ordinate represents the static light scattering intensity, and there is a positive correlation between this static light scattering intensity and the concentration of fine particles produced as the protein included in the solution aggregates. The temperature at which aggregation begins to occur is almost the same for the formulations 2-1 to 2-3; however, the amount of the fine particles produced by increasing the temperature tends to be larger as the concentration of sodium chloride is higher. Therefore, it can be said that in order to suppress the aggregation of 22KhGH-mHSA included in the solution, sucrose is preferable to sodium chloride as an excipient to be added to the aqueous pharmaceutical composition.

[Example 9] Examination 3 of Stability of Aqueous Pharmaceutical Composition Containing 22KhGH-mHSA Six kinds of aqueous pharmaceutical compositions (formulations 3-1 to 3-6) containing 35 mg/mL 22KhGH-mHSA, 20 mM phosphate buffering agent, and 70 mg/mL sucrose and having the compositions indicated in Table 4, with different concentrations of a nonionic surfactant (poloxamer 188), were prepared by using the 22KhGH-mHSA drug substance obtained in Example 6. For all the solutions, the pH was adjusted to 7.2, and the osmotic pressure ratio was adjusted to about 1.0.

TABLE 4

| Composition of aqueous pharmaceutical compositions (formulations 3-1 to 3-6) | | | | | | |
|---|---|---|---|---|---|---|
| Ingredients | Formulation 3-1 | Formulation 3-2 | Formulation 3-3 | Formulation 3-4 | Formulation 3-5 | Formulation 3-6 |
| 22KbGH-mHSA | | | | 35 mg/mL | | |
| Phosphate buffering agent | | | | 20 mM | | |
| Sucrose | | | | 70 mg/mL | | |
| Poloxamer 188 | 0 mg/mL | 0.5 mg/mL | 0.8 mg/mL | 1.0 mg/mL | 1.5 mg/mL | 2.0 mg/mL |
| Hydrochloric acid or sodium hydroxide | necessary amount | necessary amount | necessary amount | necessary amount | necessary amount | necessary amount |
| pH | | | | 7.2 | | |

1 mL each of the six kinds of aqueous pharmaceutical compositions were each filled in a glass vial, and the vials were shaken for 24 hours at a rate of 240 reciprocations/minute in a room temperature environment. The ratio occupied by the polymer in the total amount of 22KhGH-mHSA included in each solution before shaking and after shaking was measured by the SE-HPLC analysis described in Example 13, and the value obtained by subtracting the polymer content (%) before shaking from the polymer content (%) after shaking was determined as an amount of polymer increase (%). The results are presented in Table 5. Under these conditions, production of the polymer could be suppressed by setting the concentration of poloxamer 188 to be 1.0 mg/mL or higher, and the production of the polymer could be almost suppressed by setting the concentration to be 1.5 mg/mL or higher. Incidentally, in the formulation 3-1 that did not include poloxamer 188, since a large quantity of the polymer was produced, a measured value could not be obtained.

TABLE 5

| Relation between the concentration of surfactant and the influence of shaking for aqueous pharmaceutical compositions (formulations 3-1 to 3-6) | | | | | | |
|---|---|---|---|---|---|---|
| Ingredients | Formulation 3-1 | Formulation 3-2 | Formulation 3-3 | Formulation 3-4 | Formulation 3-5 | Formulation 3-6 |
| Poloxamer 188 | 0 mg/mL | 0.5 mg/mL | 0.8 mg/mL | 1.0 mg/mL | 1.5 mg/mL | 2.0 mg/mL |
| Amount at polymer increase (%) | N.D. | 13.87 | 4.46 | 0.54 | 0.06 | 0.00 |

Next, five kinds of aqueous pharmaceutical compositions (formulations 4-1 to 4-5) having the concentration of 22KhGH-mHSA set to 130 mg/mL, containing 20 mM phosphate buffering agent and 70 mg/mL sucrose, and having the compositions shown in Table 6, with different concentrations of a nonionic surfactant (poloxamer 188), were prepared. For all the solutions, the pH was adjusted to 7.2, and the osmotic pressure ratio was adjusted to about 1.0.

TABLE 6

| Composition of aqueous pharmaceutical compositions (formulations 4-1 to 4-5) | | | | | |
|---|---|---|---|---|---|
| Ingredients | Formulation 4-1 | Formulation 4-2 | Formulation 4-3 | Formulation 4-4 | Formulation 4-5 |
| 22KhGH-mHSA | | | 130 mg/mL | | |
| Phosphate buffering agent | | | 20 mM | | |
| Sucrose | | | 70 mg/mL | | |
| Poloxamer 188 | 2 mg/mL | 4 mg/mL | 6 mg/mL | 8 mg/mL | 10 mg/mL |
| Hydrochloric acid or sodium hydroxide | necessary amount | necessary amount | necessary amount | necessary amount | necessary amount |
| pH | | | 7.2 | | |

0.8 mL each of the five kinds of aqueous pharmaceutical compositions were each filled in a glass vial, and the vials were shaken for 24 hours at a rate of 240 reciprocations/minute in a room temperature environment. After shaking, the ratios occupied by the polymer and low molecular weight species in the total amount of 22KhGH-mHSA included in each solution were measured by the SE-HPLC analysis described in Example 13. The results are presented in Table 7. For all of the formulations 4-1 to 4-5, the values of the polymer content (%) and the low molecular weight species content (%) hardly changed from the values before shaking (data before shaking are not shown), and the values of the polymer content (%) and the low molecular weight species content (%) are equal in all the formulations.

TABLE 7

| Relation between the concentration of surfactant and the influence of shaking for aqueous pharmaceutical compositions (formulations 4-1 to 4-5) | | | | | |
|---|---|---|---|---|---|
| Ingredients | Formulation 4-1 | Formulation 4-2 | Formulation 4-3 | Formulation 4-4 | Formulation 4-5 |
| Poloxamer 188 | 2 mg/mL | 4 mg/mL | 8 mg/mL | 8 mg/mL | 10 mg/mL |
| Polymer content (%) | 2.18 | 2.12 | 2.09 | 2.11 | 2.13 |
| Low molecular weight species content (%) | 0.08 | 0.42 | 0.39 | 0.42 | 0.40 |

[Example 10] Examination 4 of Stability of Aqueous Pharmaceutical Composition Containing 22KhGH-mHSA Three kinds of aqueous pharmaceutical compositions (formulations 5-1 to 5-3) containing 35 mg/mL 22KhGH-mHSA, 20 mM phosphate buffering agent, 70 mg/mL sucrose, 1.0 mg/mL nonionic surfactant (poloxamer 188), and 3.3 mg/mL phenol as an antiseptic agent and having the compositions indicated in Table 8, with different pH values, were prepared by using the 22KhGH-mHSA drug substance obtained in Example 6.

TABLE 8

Composition of aqueous pharmaceutical
compositions (formulations 5-1 to 5-3)

| Ingredients | Formulation 5-1 | Formulation 5-2 | Formulation 5-3 |
|---|---|---|---|
| 22KhGH-mHSA | | 35 mg/mL | |
| Phosphate buffering agent | | 20 mM | |
| Sucrose | | 70 mg/mL | |
| Poloxamer 188 | | 1.0 mg/mL | |
| Phenol | | 3.3 mg/mL | |
| Hydrochloric acid or sodium hydroxide | necessary amount | necessary amount | necessary amount |
| pH | 6..2 | 6.7 | 7.2 |

1 mL each of the three kinds of aqueous pharmaceutical compositions were each filled in a glass vial, and the vials were left to stand and stored in a dark place for two months at 5° C. or at 25° C. The SE-HPLC analysis as described in Example 13 and the analysis of the number of fine particles as described in Example 15 were carried out after 2 weeks, after 1 month, and after 2 months for the samples left to stand at 5° C., and after one month and after two months for the samples left to stand at 25° C. The results are presented in Table 9.

In view of the polymer contents obtained by the SE-HPLC measurement, in the formulation 5-3 that was adjusted to pH: 7.2, there is almost no change in both the case where the samples were left to stand at 5° C. for one month and the case where the samples were left to stand at 25° C. for two months. On the other hand, in the formulation 5-1 adjusted to pH 6.2, a continuous increase in the content of the polymer is observed in both the case where the samples were left to stand at 5° C. for one month and the case where the samples were left to stand at 25° C. for 2 months. Furthermore, in the formulation 5-2 adjusted to pH 6.7, there is no change in the content of the polymer when the samples were left to stand at 5° C. for one month; however, when the samples were left to stand at 25° C. for two months, a continuous increase in the polymer is observed. In view of the low molecular weight species content obtained by SE-HPLC measurement, when the samples were left to stand at 5° C. for one month, there is almost no change in all the formulations 5-1 to 5-3. On the other hand, when the samples were left to stand at 25° C. for two months, an increase in the low molecular weight species content is observed in all the formulations; however, the extent of the increase is negligible. In view of the analysis of the number of fine particles, in the formulation 5-3 adjusted to pH 7.2, the numbers of fine particles having a size of 10 μm or more and a size of 25 μm or more have been significantly decreased as compared with the formulations 5-1 and 5-2.

TABLE 9

Results of stability study for aqueous pharmaceutical compositions (formulations 5-1 to 5-3)

| Evaluations items | | Formulations | Immediately after preparation | 5° C. 2 W | 5° C. 1 M | 5° C. 2 M | 25° C. 1 M | 25° C. 2 M |
|---|---|---|---|---|---|---|---|---|
| SE-HPLC analysis | Polymer content (%) | 5-1 | 1.69 | 1.80 | 1.85 | 1.99 | 2.12 | 2.25 |
| | | 5-2 | 1.68 | 1.79 | 1.83 | 1.85 | 1.87 | 1.92 |
| | | 5-3 | 1.72 | 1.81 | 1.83 | 1.83 | 1.77 | 1.80 |
| | Low molecular weight species content (%) | 5-1 | 0.12 | 0.12 | 0.15 | 0.13 | 0.32 | 0.42 |
| | | 5-2 | 0.13 | 0.14 | 0.15 | 0.14 | 0.36 | 0.49 |
| | | 5-3 | 0.12 | 0.14 | 0.16 | 0.15 | 0.41 | 0.55 |
| Number of fine particles (particles/mL) | 10 μm or more | 5-1 | 34 | 51 | 820 | 957 | 222 | 684 |
| | 25 μm or more | | 17 | 17 | 68 | 34 | 0 | 51 |
| | 10 μm or more | 5-2 | 34 | 17 | 1266 | 325 | 461 | 736 |
| | 25 μm or more | | 0 | 0 | 188 | 51 | 51 | 68 |
| | 10 μm or more | 5-3 | 34 | 34 | 205 | 188 | 103 | 34 |
| | 25 μm or more | | 0 | 0 | 17 | 34 | 0 | 0 |

[Example 11] Preparation Design of Aqueous Pharmaceutical Composition

Prom the results shown in the above-described Examples 7 to 10, a preparation formulation having the composition shown in Table 10 (formulation 6) can be designed, which contains 50 mg/mL 22KhGH-mHSA, 10 mM phosphate buffering agent, 75 mg/mL sucrose, 3 mg/mL poloxamer 188, and 6 mg/mL phenol and has the pH adjusted to 7.2 and the osmotic pressure ratio adjusted to about 1.0, as a suitable example of the preparation formulation of the aqueous pharmaceutical composition containing 22KhGH-mHSA. This aqueous pharmaceutical composition can be filled and encapsulated in a vial, an ampoule, or a syringe, each made of glass or plastic, in a liquid amount of 0.5 to 10 mL. An aqueous pharmaceutical composition that has been prefilled in a syringe may be supplied as a prefilled preparation. The storage temperature is preferably 2° C. to 10° C., for example, 4° C., and storage in a refrigerator where temperature recording is possible is assumed.

TABLE 10

| Composition of aqueous pharmaceutical composition (formulation 6) | |
| --- | --- |
| Ingredients | Formulation 6 |
| 22KhGH-mHSA | 50 mg/mL |
| Phosphate buffering agent | 10 mM |
| Sucrose | 75 mg/mL |
| Poloxamer 188 | 3 mg/mL |
| Phenol | 6 mg/mL |
| Hydrochloric acid or sodium hydroxide | necessary amount |
| pH | 7.2 |

[Example 12] Examination 5 of Stability of Aqueous Pharmaceutical Composition Containing 22KhGH-mHSA The aqueous pharmaceutical composition of formulation 6 having the composition shown in Table 10 was prepared, 1.7 mL of the composition was filled in a borosilicate glass cartridge, and the cartridge was left to stand and stored in a dark place at 5° C. for 12 months. After 3 months, after 6 months, and after 12 months, the property test described in Example 14, the insoluble foreign matter test and pH measurement described in Example 16, the SE-HPLC analysis described in Example 13, the analysis of the number of fine particles described in Example 15, and the 22KhGH-mHSA quantification described in Example 17 were carried out. The results are presented in Table 11. There is no significant change in any of the examined values, and it can be seen that the formulation 6 is stable for at least 12 months as an aqueous pharmaceutical composition containing 22KhGH-mHSA. Incidentally, in Table 11, the 22KhGH-mHSA quantification (against theoretical value (%)) indicates the actual quantification value (%) when the amount of 22KhGH-mHSA at the time of preparing the formulation 6 was taken as 100%.

[Example 13] SE-HPLC Analysis (Measurement of Contents of Polymer, Monomer, and Low Molecular Weight Species of 22KhGH-mHSA Using SE-HPLC)

Sodium dihydrogen phosphate dihydrate and sodium chloride were dissolved in water, and a phosphate buffer solution containing 0.1 M phosphoric acid and 0.2 M sodium chloride was prepared. Furthermore, a solution that had the same composition as each of the aqueous pharmaceutical compositions to be tested and did not include 22KhGH-mHSA and phenol was prepared, and this was used as a sample diluent.

An aqueous pharmaceutical composition to be tested was adjusted using the sample diluent so as to obtain a protein concentration of 2.0 mg/mL, and the resultant was used as a sample solution.

Figure 2:
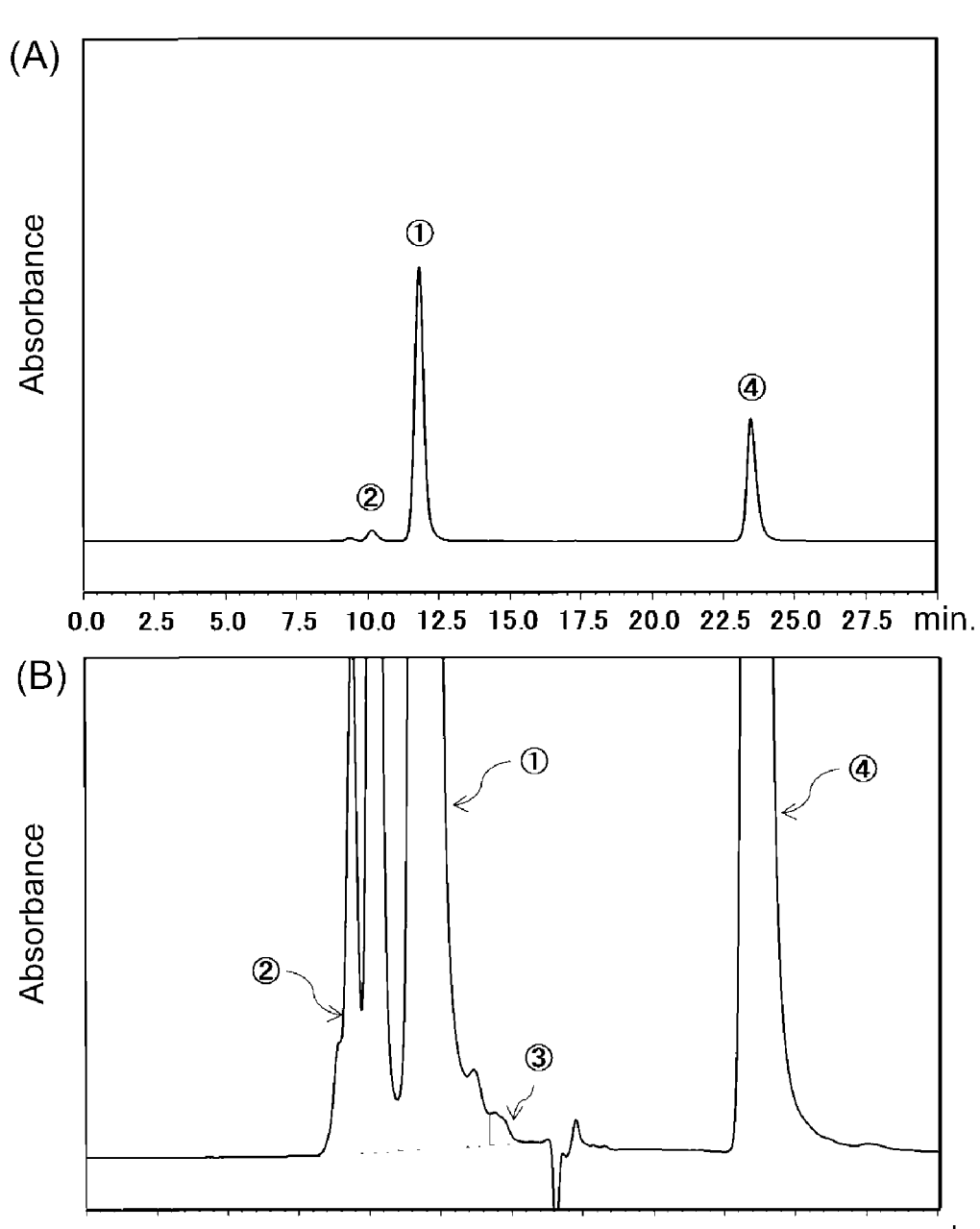
FIG. 2A shows an SE-HPLC chart immediately after the preparation of formulation 5-1 in Example 10. The axis of ordinate represents the absorbance (arbitrary unit) at 215 nm, and the axis of abscissa represents the retention time (minutes).
FIG. 2B is an enlarged view of FIG. 2A in the direction of the axis of ordinate. In the drawing, peak 1 corresponds to a monomer of 22KhGH-mHSA, peak 2 corresponds to a polymer thereof, peak 3 corresponds to low molecular weight species thereof, and peak 4 corresponds to phenol.

Measurement was carried out by using an HPLC apparatus (LC-20A, Shimadzu Corp.) and a column (TSKgel G3000SW$_{XL}$, Tosoh Corp.) under the conditions shown in the following Table 12. However, the flow rate was not necessarily limited to the conditions shown in Table 12 and was appropriately adjusted such that the retention time of the main peak was near 12 minutes. A representative chromatogram is shown in FIG. 2. In the chromatogram obtained by measurement of a sample solution, a main peak detected near a retention time of 12 minutes was designated as monomer, a peak detected before the main peak was designated as polymer, a peak detected after the main peak was designated as low molecular weight species, and the main peak content (%), the polymer content (%), and the low molecular weight species content (%) were calculated from the areas of the respective peaks. Incidentally, since the peak detected near 23.5 minutes was derived from phenol, the peak was excluded from the analysis. Furthermore, a peak that was the same as the peak detected on the chromatogram obtained by measurement of the sample diluent was also excluded from the analysis of the sample solution.

TABLE 11

| Results of stability study for cartridge composition of aqueous pharmaceutical composition (formulation 6) | | | | | |
| --- | --- | --- | --- | --- | --- |
| | | Evaluation Items | | | |
| | | Immediately after preparation | 5° C. 3 M | 5° C. 6 M | 5° C. 12 M |
| Property test | | brownish yellow clear solution | brownish yellow clear solution | brownish yellow clear solution | brownish yellow clear solution |
| Insoluble foreign matter test | | not detected | not detected | not detected | not detected |
| Measured pH | | 7.21 | 7.17 | 7.20 | 7.18 |
| SE-HPLC analysis | Monomer content (%) | 98.4 | 98.2 | 98.4 | 97.6 |
| | Polymer content (%) | 1.31 | 1.47 | 1.49 | 1.89 |
| | Low molecular weight species content (%) | 0.33 | 0.31 | 0.07 | 0.50 |
| Number of fine particles (particles/mL) | 10 μm or more | 179 | 11 | 184 | 40 |
| | 25 μm or more | 100 | 0 | 6 | 6 |
| 22KhGH-mHSA quantification (against theoretical value(%)) | | 102 | 102 | 100 | 102 |

TABLE 12

| Conditions of SE-HPLC measurement | |
| --- | --- |
| Detector | Ultraviolet absorptiometer (wavelength 215 nm) |
| Cell temperature | 40° C. |
| Column temperature | 25° C. |
| Auto sampler temperature | 4° C. |
| Flow rate | 0.7 mL/min |
| Range of retention time for calculating peak area on chromatogram | 30 minutes after injection of the sample to be measured |

[Example 14] Property Test

As liquid for color comparison, the following were used.

(1) Color Reference Solutions set B (brown, Sigma-Aldrich Corp.)

(2) Color Reference Solutions set BY (brownish yellow, Sigma-Aldrich Corp.)

(3) Color Reference Solutions set Y (yellow, Sigma-Aldrich Corp.)

A container (vial or the like) containing an aqueous pharmaceutical composition to be tested was observed from a side surface of the container by using a black background and a white background, and the color tone and clarity were checked. Upon determination of the color none, the liquids for color comparison were allowed to be used.

[Example 15] Measurement of Number of Fine Particles

Measurement conditions: Measurement was carried out under the conditions shown in the following Table 13 by using a FlowSight particle image analyzer (FlowCam VS-1, FLUID IMAGING TECHNOLOGIES, Inc.). The number of fine particles (particles/mL) included in the aqueous pharmaceutical composition to be tested was performed by using a flow cell (FC80FV-5, FLUID IMAGING TECHNOLO-GIES, Inc.). Regarding the number of fine particles, the numbers of particles having a diameter of 10 μm or more and particles having a diameter of 25 μm or more were each measured.

TABLE 13

| Measurement conditions of number of fine particles | |
| --- | --- |
| Sample Volume | 100 μL |
| Distance to Nearest Neighbor | 0 μm |
| Flow Rate | 0.05 mL/min |
| AutoImage Rate | 22 frames per second |

[Example 16] Methods for Insoluble Foreign Matter Examination, pH, Measurement, and Osmotic Pressure Ratio Measurement The insoluble foreign matter examination, the pH measurement, and the osmotic pressure ratio measurement were carried out by the general techniques specified in the Japanese Pharmacopoeia. Incidentally, the insoluble foreign matter examination is an examination method of checking the presence or absence of insoluble foreign matter that is easily detected, by visual inspection.

[Example 17] Quantification of 22KhGH-mHSA (Bradford Method)

A 22KhGH-mHSA solution having a known concentration was diluted with water to prepare solutions containing 22KhGH-mHSA at concentrations of 1.0, 0.8, 0.6, 0.4, and 0.2 mg/mL, respectively, were prepared, and these were designated as standard solutions 1 to 5, respectively. An aqueous pharmaceutical composition to be tested was diluted with water such that the protein concentration was within the range of 0.4 to 0.8 mg/mL, and the dilution was used as a sample solution.

Reaction caused by Coomassie reagent: 5 mL each of the Pierce Coomassie Assay Reagent included in PIERCE™ Coomassie (Bradford) Protein Assay Kit (Thermo Fisher SCIENTIFIC, Inc.) was collected in a 15-mL centrifuge tube for the number required for measurement. Next, 100 L each of water (for blank), each of the standard solutions 1 to 5, and a sample solution were each added to a 15-mL centrifuge tube containing the collected Pierce Coomassie Assay Reagent, and mixture was inverted and mixed and then left to stand for 10 minutes at room temperature to react. After the reaction, 2 mL or more of the measurement sample was rapidly introduced into a measurement cell (cuvette, optical path length 10 mm, optical path width 10 mm, Sarstedt K.K.), and absorbance measurement at a wavelength of 595 nm was carried out by using a spectrophotometer (UV-2600, Shimadzu Corp.). A regression line (calibration curve) was produced by plotting the absorbance of the standard solutions 1 to 5 on the Y-axis and plotting the theoretical protein concentration on the X-axis, and the protein concentration was calculated from the absorbance of the sample solution.

INDUSTRIAL APPLICABILITY

According to the present invention, a medicine containing a protein in which serum albumin and growth hormone are coupled, as an active ingredient, can be distributed in the market in the form of an aqueous pharmaceutical composition.

SEQUENCE LISTING FREE TEXT

SEQ ID NO:1: Amino acid sequence of wild-type human serum albumin

SEQ ID NO:2: Amino acid sequence of human serum albumin Redhill

SEQ ID NO:3: Amino acid sequence of human serum albumin mutant (A320T)

SEQ ID NO:4: Example 1 of linker amino acid sequence

SEQ ID NO:5: Example 2 of linker amino acid sequence

SEQ ID NO:6: Example 3 of linker amino acid sequence

SEQ ID NO:7: Partial base sequence of wild-type mouse encephalomyelitis virus-derived internal ribosome entry site SEQ ID NO:8: Partial base sequence of mutant mouse encephalomyelitis virus-derived internal ribosome entry site, synthesized SEQ ID NO:9: Amino acid sequence of 22K human growth hormone SEQ ID NO:10: Amino acid sequence of 20K human growth hormone SEQ ID NO:11: Amino acid sequence of 22KhGH-mHSA SEQ ID NO:12: Amino acid sequence of 20KhGH-mHSA SEQ ID NO:13: Primer YA082, synthetic sequence SEQ ID NO:14: Primer YA083, synthetic sequence SEQ ID NO:15: Amino acid sequence of 22KhGH-HSA SEQ ID NO:16: Base sequence including 22KhGH-HSA gene, synthetic sequence

SEQUENCE LISTING

1226JP_ST25.TXT

---

US 12,685,762 B2

69

70

The invention claimed is:

1. An aqueous pharmaceutical composition, comprising:
a fusion protein of human serum albumin and human growth hormone as an active ingredient at a concentration of 50 mg/mL;
sucrose at a concentration of 75 mg/mL;
a nonionic surfactant at a concentration of 3 mg/mL;
an antiseptic agent at a concentration of 6 mg/mL; and
a buffering agent at a concentration of 10 mM,
wherein a pH is 7.0 to 7.4,
wherein
the nonionic surfactant is polyoxyethylene (160) poly-oxypropylene (30) glycol,
the antiseptic agent is phenol,
the buffering agent is a phosphate buffering agent, and
the fusion protein has the amino acid sequence of SEQ ID NO:11.

* * * * *

```
                             SEQUENCE LISTING

<160> NUMBER OF SEQ ID NOS: 16

<210> SEQ ID NO 1
<211> LENGTH: 585
<212> TYPE: PRT
<213> ORGANISM: Homo sapiens

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
```

-continued

```
              340              345              350

Tyr Glu Thr Thr Leu Glu Lys Cys Cys Ala Ala Ala Asp Pro His Glu
          355              360              365

Cys Tyr Ala Lys Val Phe Asp Glu Phe Lys Pro Leu Val Glu Glu Pro
      370              375              380

Gln Asn Leu Ile Lys Gln Asn Cys Glu Leu Phe Glu Gln Leu Gly Glu
385              390              395              400

Tyr Lys Phe Gln Asn Ala Leu Leu Val Arg Tyr Thr Lys Lys Val Pro
              405              410              415

Gln Val Ser Thr Pro Thr Leu Val Glu Val Ser Arg Asn Leu Gly Lys
              420              425              430

Val Gly Ser Lys Cys Cys Lys His Pro Glu Ala Lys Arg Met Pro Cys
              435              440              445

Ala Glu Asp Tyr Leu Ser Val Val Leu Asn Gln Leu Cys Val Leu His
          450              455              460

Glu Lys Thr Pro Val Ser Asp Arg Val Thr Lys Cys Cys Thr Glu Ser
465              470              475              480

Leu Val Asn Arg Arg Pro Cys Phe Ser Ala Leu Glu Val Asp Glu Thr
              485              490              495

Tyr Val Pro Lys Glu Phe Asn Ala Glu Thr Phe Thr Phe His Ala Asp
              500              505              510

Ile Cys Thr Leu Ser Glu Lys Glu Arg Gln Ile Lys Lys Gln Thr Ala
          515              520              525

Leu Val Glu Leu Val Lys His Lys Pro Lys Ala Thr Lys Glu Gln Leu
          530              535              540

Lys Ala Val Met Asp Asp Phe Ala Ala Phe Val Glu Lys Cys Cys Lys
545              550              555              560

Ala Asp Asp Lys Glu Thr Cys Phe Ala Glu Glu Gly Lys Lys Leu Val
              565              570              575

Ala Ala Ser Gln Ala Ala Leu Gly Leu
              580              585

<210> SEQ ID NO 2
<211> LENGTH: 586
<212> TYPE: PRT
<213> ORGANISM: Homo sapiens

<400> SEQUENCE: 2

Arg Asp Ala His Lys Ser Glu Val Ala His Arg Phe Lys Asp Leu Gly
1                5               10               15

Glu Glu Asn Phe Lys Ala Leu Val Leu Ile Ala Phe Ala Gln Tyr Leu
              20               25               30

Gln Gln Cys Pro Phe Glu Asp His Val Lys Leu Val Asn Glu Val Thr
          35               40               45

Glu Phe Ala Lys Thr Cys Val Ala Asp Glu Ser Ala Glu Asn Cys Asp
      50               55               60

Lys Ser Leu His Thr Leu Phe Gly Asp Lys Leu Cys Thr Val Ala Thr
65               70               75               80

Leu Arg Glu Thr Tyr Gly Glu Met Ala Asp Cys Cys Ala Lys Gln Glu
              85               90               95

Pro Glu Arg Asn Glu Cys Phe Leu Gln His Lys Asp Asp Asn Pro Asn
              100              105              110

Leu Pro Arg Leu Val Arg Pro Glu Val Asp Val Met Cys Thr Ala Phe
          115              120              125
```

```
His Asp Asn Glu Glu Thr Phe Leu Lys Lys Tyr Leu Tyr Glu Ile Ala
    130                 135                 140

Arg Arg His Pro Tyr Phe Tyr Ala Pro Glu Leu Leu Phe Phe Ala Lys
145                 150                 155                 160

Arg Tyr Lys Ala Ala Phe Thr Glu Cys Cys Gln Ala Ala Asp Lys Ala
                165                 170                 175

Ala Cys Leu Leu Pro Lys Leu Asp Glu Leu Arg Asp Glu Gly Lys Ala
            180                 185                 190

Ser Ser Ala Lys Gln Arg Leu Lys Cys Ala Ser Leu Gln Lys Phe Gly
        195                 200                 205

Glu Arg Ala Phe Lys Ala Trp Ala Val Ala Arg Leu Ser Gln Arg Phe
    210                 215                 220

Pro Lys Ala Glu Phe Ala Glu Val Ser Lys Leu Val Thr Asp Leu Thr
225                 230                 235                 240

Lys Val His Thr Glu Cys Cys His Gly Asp Leu Leu Glu Cys Ala Asp
                245                 250                 255

Asp Arg Ala Asp Leu Ala Lys Tyr Ile Cys Glu Asn Gln Asp Ser Ile
            260                 265                 270

Ser Ser Lys Leu Lys Glu Cys Cys Glu Lys Pro Leu Leu Glu Lys Ser
        275                 280                 285

His Cys Ile Ala Glu Val Glu Asn Asp Glu Met Pro Ala Asp Leu Pro
    290                 295                 300

Ser Leu Ala Ala Asp Phe Val Glu Ser Lys Asp Val Cys Lys Asn Tyr
305                 310                 315                 320

Thr Glu Ala Lys Asp Val Phe Leu Gly Met Phe Leu Tyr Glu Tyr Ala
                325                 330                 335

Arg Arg His Pro Asp Tyr Ser Val Val Leu Leu Leu Arg Leu Ala Lys
            340                 345                 350

Thr Tyr Glu Thr Thr Leu Glu Lys Cys Cys Ala Ala Ala Asp Pro His
        355                 360                 365

Glu Cys Tyr Ala Lys Val Phe Asp Glu Phe Lys Pro Leu Val Glu Glu
    370                 375                 380

Pro Gln Asn Leu Ile Lys Gln Asn Cys Glu Leu Phe Glu Gln Leu Gly
385                 390                 395                 400

Glu Tyr Lys Phe Gln Asn Ala Leu Leu Val Arg Tyr Thr Lys Lys Val
                405                 410                 415

Pro Gln Val Ser Thr Pro Thr Leu Val Glu Val Ser Arg Asn Leu Gly
            420                 425                 430

Lys Val Gly Ser Lys Cys Cys Lys His Pro Glu Ala Lys Arg Met Pro
        435                 440                 445

Cys Ala Glu Asp Tyr Leu Ser Val Val Leu Asn Gln Leu Cys Val Leu
    450                 455                 460

His Glu Lys Thr Pro Val Ser Asp Arg Val Thr Lys Cys Cys Thr Glu
465                 470                 475                 480

Ser Leu Val Asn Arg Arg Pro Cys Phe Ser Ala Leu Glu Val Asp Glu
                485                 490                 495

Thr Tyr Val Pro Lys Glu Phe Asn Ala Glu Thr Phe Thr Phe His Ala
            500                 505                 510

Asp Ile Cys Thr Leu Ser Glu Lys Glu Arg Gln Ile Lys Lys Gln Thr
        515                 520                 525

Ala Leu Val Glu Leu Val Lys His Lys Pro Lys Ala Thr Lys Glu Gln
    530                 535                 540

Leu Lys Ala Val Met Asp Asp Phe Ala Ala Phe Val Glu Lys Cys Cys
```

-continued

```
545                  550                  555                  560

Lys Ala Asp Asp Lys Glu Thr Cys Phe Ala Glu Glu Gly Lys Lys Leu
                565                  570                  575

Val Ala Ala Ser Gln Ala Ala Leu Gly Leu
            580                  585
```

```
<210> SEQ ID NO 3
<211> LENGTH: 585
<212> TYPE: PRT
<213> ORGANISM: Artificial Sequence
<220> FEATURE:
<223> OTHER INFORMATION: Amino acid sequence of human serum albumin
      mutant (A320T)

<400> SEQUENCE: 3

Asp Ala His Lys Ser Glu Val Ala His Arg Phe Lys Asp Leu Gly Glu
1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Thr
305                 310                 315                 320
```

-continued

```
Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585
```

```
<210> SEQ ID NO 4
<211> LENGTH: 5
<212> TYPE: PRT
<213> ORGANISM: Artificial Sequence
<220> FEATURE:
<223> OTHER INFORMATION: Amino acid sequence of an exemplified linker 1

<400> SEQUENCE: 4

Gly Gly Gly Gly Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Amino acid sequence of an exemplified linker 2

<400> SEQUENCE: 5

Gly Gly Gly Gly Gly Ser
1               5

<210> SEQ ID NO 6
```

```
<211> LENGTH: 5
<212> TYPE: PRT
<213> ORGANISM: Artificial Sequence
<220> FEATURE:
<223> OTHER INFORMATION: Amino acid sequence of an exemplified linker 3

<400> SEQUENCE: 6

Ser Gly Gly Gly Gly
1               5

<210> SEQ ID NO 7
<211> LENGTH: 23
<212> TYPE: DNA
<213> ORGANISM: Murine encephalomyocardinitis virus

<400> SEQUENCE: 7 atgataaatat ggccacaacc atg                                          23

<210> SEQ ID NO 8
<211> LENGTH: 23
<212> TYPE: DNA
<213> ORGANISM: Artificial Sequence
<220> FEATURE:
<223> OTHER INFORMATION: Partial nucleotide sequence of IRES from mutant
      type murine encephalomyocardinitis virus

<400> SEQUENCE: 8
atgataagct tgccacaacc atg                                           23

<210> SEQ ID NO 9
<211> LENGTH: 191
<212> TYPE: PRT
<213> ORGANISM: Homo sapiens

<400> SEQUENCE: 9

Phe Pro Thr Ile Pro Leu Ser Arg Leu Phe Asp Asn Ala Met Leu Arg
1               5               10              15

Ala His Arg Leu His Gln Leu Ala Phe Asp Thr Tyr Gln Glu Phe Glu
            20              25              30

Glu Ala Tyr Ile Pro Lys Glu Gln Lys Tyr Ser Phe Leu Gln Asn Pro
        35              40              45

Gln Thr Ser Leu Cys Phe Ser Glu Ser Ile Pro Thr Pro Ser Asn Arg
    50              55              60

Glu Glu Thr Gln Gln Lys Ser Asn Leu Glu Leu Leu Arg Ile Ser Leu
65              70              75              80

Leu Leu Ile Gln Ser Trp Leu Glu Pro Val Gln Phe Leu Arg Ser Val
                85              90              95

Phe Ala Asn Ser Leu Val Tyr Gly Ala Ser Asp Ser Asn Val Tyr Asp
            100             105             110

Leu Leu Lys Asp Leu Glu Glu Gly Ile Gln Thr Leu Met Gly Arg Leu
        115             120             125

Glu Asp Gly Ser Pro Arg Thr Gly Gln Ile Phe Lys Gln Thr Tyr Ser
        130             135             140

Lys Phe Asp Thr Asn Ser His Asn Asp Asp Ala Leu Leu Lys Asn Tyr
145             150             155             160

Gly Leu Leu Tyr Cys Phe Arg Lys Asp Met Asp Lys Val Glu Thr Phe
                165             170             175

Leu Arg Ile Val Gln Cys Arg Ser Val Glu Gly Ser Cys Gly Phe
            180             185             190
```

```
<210> SEQ ID NO 10
<211> LENGTH: 176
<212> TYPE: PRT
<213> ORGANISM: Homo sapiens

<400> SEQUENCE: 10

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Asn
            20                  25                  30

Pro Gln Thr Ser Leu Cys Phe Ser Glu Ser Ile Pro Thr Pro Ser Asn
            35                  40                  45

Arg Glu Glu Thr Gln Gln Lys Ser Asn Leu Glu Leu Leu Arg Ile Ser
        50                  55                  60

Leu Leu Leu Ile Gln Ser Trp Leu Glu Pro Val Gln Phe Leu Arg Ser
65                  70                  75                  80

Val Phe Ala Asn Ser Leu Val Tyr Gly Ala Ser Asp Ser Asn Val Tyr
                85                  90                  95

Asp Leu Leu Lys Asp Leu Glu Glu Gly Ile Gln Thr Leu Met Gly Arg
            100                 105                 110

Leu Glu Asp Gly Ser Pro Arg Thr Gly Gln Ile Phe Lys Gln Thr Tyr
            115                 120                 125

Ser Lys Phe Asp Thr Asn Ser His Asn Asp Asp Ala Leu Leu Lys Asn
        130                 135                 140

Tyr Gly Leu Leu Tyr Cys Phe Arg Lys Asp Met Asp Lys Val Glu Thr
145                 150                 155                 160

Phe Leu Arg Ile Val Gln Cys Arg Ser Val Glu Gly Ser Cys Gly Phe
                165                 170                 175

<210> SEQ ID NO 11
<211> LENGTH: 776
<212> TYPE: PRT
<213> ORGANISM: Artificial Sequence
<220> FEATURE:
<223> OTHER INFORMATION: Amino acid sequence of 22KhGH-mHSA

<400> SEQUENCE: 11

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
        130                 135                 140

Lys Phe Asp Thr Asn Ser His Asn Asp Asp Ala Leu Leu Lys Asn Tyr
145                 150                 155                 160
```

```
Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Asp
            180                 185                 190

Ala His Lys Ser Glu Val Ala His Arg Phe Lys Asp Leu Gly Glu Glu
        195                 200                 205

Asn Phe Lys Ala Leu Val Leu Ile Ala Phe Ala Gln Tyr Leu Gln Gln
    210                 215                 220

Cys Pro Phe Glu Asp His Val Lys Leu Val Asn Glu Val Thr Glu Phe
225                 230                 235                 240

Ala Lys Thr Cys Val Ala Asp Glu Ser Ala Glu Asn Cys Asp Lys Ser
                245                 250                 255

Leu His Thr Leu Phe Gly Asp Lys Leu Cys Thr Val Ala Thr Leu Arg
            260                 265                 270

Glu Thr Tyr Gly Glu Met Ala Asp Cys Cys Ala Lys Gln Glu Pro Glu
        275                 280                 285

Arg Asn Glu Cys Phe Leu Gln His Lys Asp Asp Asn Pro Asn Leu Pro
    290                 295                 300

Arg Leu Val Arg Pro Glu Val Asp Val Met Cys Thr Ala Phe His Asp
305                 310                 315                 320

Asn Glu Glu Thr Phe Leu Lys Lys Tyr Leu Tyr Glu Ile Ala Arg Arg
                325                 330                 335

His Pro Tyr Phe Tyr Ala Pro Glu Leu Leu Phe Phe Ala Lys Arg Tyr
            340                 345                 350

Lys Ala Ala Phe Thr Glu Cys Cys Gln Ala Ala Asp Lys Ala Ala Cys
        355                 360                 365

Leu Leu Pro Lys Leu Asp Glu Leu Arg Asp Glu Gly Lys Ala Ser Ser
    370                 375                 380

Ala Lys Gln Arg Leu Lys Cys Ala Ser Leu Gln Lys Phe Gly Glu Arg
385                 390                 395                 400

Ala Phe Lys Ala Trp Ala Val Ala Arg Leu Ser Gln Arg Phe Pro Lys
                405                 410                 415

Ala Glu Phe Ala Glu Val Ser Lys Leu Val Thr Asp Leu Thr Lys Val
            420                 425                 430

His Thr Glu Cys Cys His Gly Asp Leu Leu Glu Cys Ala Asp Asp Arg
        435                 440                 445

Ala Asp Leu Ala Lys Tyr Ile Cys Glu Asn Gln Asp Ser Ile Ser Ser
    450                 455                 460

Lys Leu Lys Glu Cys Cys Glu Lys Pro Leu Leu Glu Lys Ser His Cys
465                 470                 475                 480

Ile Ala Glu Val Glu Asn Asp Glu Met Pro Ala Asp Leu Pro Ser Leu
                485                 490                 495

Ala Ala Asp Phe Val Glu Ser Lys Asp Val Cys Lys Asn Tyr Thr Glu
            500                 505                 510

Ala Lys Asp Val Phe Leu Gly Met Phe Leu Tyr Glu Tyr Ala Arg Arg
        515                 520                 525

His Pro Asp Tyr Ser Val Val Leu Leu Leu Arg Leu Ala Lys Thr Tyr
    530                 535                 540

Glu Thr Thr Leu Glu Lys Cys Cys Ala Ala Ala Asp Pro His Glu Cys
545                 550                 555                 560

Tyr Ala Lys Val Phe Asp Glu Phe Lys Pro Leu Val Glu Glu Pro Gln
                565                 570                 575
```

-continued

```
Asn Leu Ile Lys Gln Asn Cys Glu Leu Phe Glu Gln Leu Gly Glu Tyr
            580             585             590

Lys Phe Gln Asn Ala Leu Leu Val Arg Tyr Thr Lys Lys Val Pro Gln
        595             600             605

Val Ser Thr Pro Thr Leu Val Glu Val Ser Arg Asn Leu Gly Lys Val
    610             615             620

Gly Ser Lys Cys Cys Lys His Pro Glu Ala Lys Arg Met Pro Cys Ala
625             630             635             640

Glu Asp Tyr Leu Ser Val Val Leu Asn Gln Leu Cys Val Leu His Glu
            645             650             655

Lys Thr Pro Val Ser Asp Arg Val Thr Lys Cys Cys Thr Glu Ser Leu
            660             665             670

Val Asn Arg Arg Pro Cys Phe Ser Ala Leu Glu Val Asp Glu Thr Tyr
            675             680             685

Val Pro Lys Glu Phe Asn Ala Glu Thr Phe Thr Phe His Ala Asp Ile
    690             695             700

Cys Thr Leu Ser Glu Lys Glu Arg Gln Ile Lys Lys Gln Thr Ala Leu
705             710             715             720

Val Glu Leu Val Lys His Lys Pro Lys Ala Thr Lys Glu Gln Leu Lys
            725             730             735

Ala Val Met Asp Asp Phe Ala Ala Phe Val Glu Lys Cys Cys Lys Ala
            740             745             750

Asp Asp Lys Glu Thr Cys Phe Ala Glu Glu Gly Lys Lys Leu Val Ala
            755             760             765

Ala Ser Gln Ala Ala Leu Gly Leu
    770             775
```

```
<210> SEQ ID NO 12
<211> LENGTH: 761
<212> TYPE: PRT
<213> ORGANISM: Artificial Sequence
<220> FEATURE:
<223> OTHER INFORMATION: Amino acid sequence of 20KhGH-mHSA

<400> SEQUENCE: 12
```

```
Phe Pro Thr Ile Pro Leu Ser Arg Leu Phe Asp Asn Ala Met Leu Arg
1           5               10              15

Ala His Arg Leu His Gln Leu Ala Phe Asp Thr Tyr Gln Glu Phe Asn
            20              25              30

Pro Gln Thr Ser Leu Cys Phe Ser Glu Ser Ile Pro Thr Pro Ser Asn
            35              40              45

Arg Glu Glu Thr Gln Gln Lys Ser Asn Leu Glu Leu Leu Arg Ile Ser
    50              55              60

Leu Leu Leu Ile Gln Ser Trp Leu Glu Pro Val Gln Phe Leu Arg Ser
65              70              75              80

Val Phe Ala Asn Ser Leu Val Tyr Gly Ala Ser Asp Ser Asn Val Tyr
            85              90              95

Asp Leu Leu Lys Asp Leu Glu Glu Gly Ile Gln Thr Leu Met Gly Arg
            100             105             110

Leu Glu Asp Gly Ser Pro Arg Thr Gly Gln Ile Phe Lys Gln Thr Tyr
            115             120             125

Ser Lys Phe Asp Thr Asn Ser His Asn Asp Asp Ala Leu Leu Lys Asn
    130             135             140

Tyr Gly Leu Leu Tyr Cys Phe Arg Lys Asp Met Asp Lys Val Glu Thr
145             150             155             160
```

-continued

```
Phe Leu Arg Ile Val Gln Cys Arg Ser Val Glu Gly Ser Cys Gly Phe
            165                 170                 175

Asp Ala His Lys Ser Glu Val Ala His Arg Phe Lys Asp Leu Gly Glu
            180                 185                 190

Glu Asn Phe Lys Ala Leu Val Leu Ile Ala Phe Ala Gln Tyr Leu Gln
            195                 200                 205

Gln Cys Pro Phe Glu Asp His Val Lys Leu Val Asn Glu Val Thr Glu
    210                 215                 220

Phe Ala Lys Thr Cys Val Ala Asp Glu Ser Ala Glu Asn Cys Asp Lys
225                 230                 235                 240

Ser Leu His Thr Leu Phe Gly Asp Lys Leu Cys Thr Val Ala Thr Leu
            245                 250                 255

Arg Glu Thr Tyr Gly Glu Met Ala Asp Cys Cys Ala Lys Gln Glu Pro
            260                 265                 270

Glu Arg Asn Glu Cys Phe Leu Gln His Lys Asp Asp Asn Pro Asn Leu
            275                 280                 285

Pro Arg Leu Val Arg Pro Glu Val Asp Val Met Cys Thr Ala Phe His
    290                 295                 300

Asp Asn Glu Glu Thr Phe Leu Lys Lys Tyr Leu Tyr Glu Ile Ala Arg
305                 310                 315                 320

Arg His Pro Tyr Phe Tyr Ala Pro Glu Leu Leu Phe Phe Ala Lys Arg
            325                 330                 335

Tyr Lys Ala Ala Phe Thr Glu Cys Cys Gln Ala Ala Asp Lys Ala Ala
            340                 345                 350

Cys Leu Leu Pro Lys Leu Asp Glu Leu Arg Asp Glu Gly Lys Ala Ser
            355                 360                 365

Ser Ala Lys Gln Arg Leu Lys Cys Ala Ser Leu Gln Lys Phe Gly Glu
    370                 375                 380

Arg Ala Phe Lys Ala Trp Ala Val Ala Arg Leu Ser Gln Arg Phe Pro
385                 390                 395                 400

Lys Ala Glu Phe Ala Glu Val Ser Lys Leu Val Thr Asp Leu Thr Lys
            405                 410                 415

Val His Thr Glu Cys Cys His Gly Asp Leu Leu Glu Cys Ala Asp Asp
            420                 425                 430

Arg Ala Asp Leu Ala Lys Tyr Ile Cys Glu Asn Gln Asp Ser Ile Ser
            435                 440                 445

Ser Lys Leu Lys Glu Cys Cys Glu Lys Pro Leu Leu Glu Lys Ser His
    450                 455                 460

Cys Ile Ala Glu Val Glu Asn Asp Glu Met Pro Ala Asp Leu Pro Ser
465                 470                 475                 480

Leu Ala Ala Asp Phe Val Glu Ser Lys Asp Val Cys Lys Asn Tyr Thr
            485                 490                 495

Glu Ala Lys Asp Val Phe Leu Gly Met Phe Leu Tyr Glu Tyr Ala Arg
            500                 505                 510

Arg His Pro Asp Tyr Ser Val Val Leu Leu Leu Arg Leu Ala Lys Thr
            515                 520                 525

Tyr Glu Thr Thr Leu Glu Lys Cys Cys Ala Ala Ala Asp Pro His Glu
    530                 535                 540

Cys Tyr Ala Lys Val Phe Asp Glu Phe Lys Pro Leu Val Glu Glu Pro
545                 550                 555                 560

Gln Asn Leu Ile Lys Gln Asn Cys Glu Leu Phe Glu Gln Leu Gly Glu
            565                 570                 575

Tyr Lys Phe Gln Asn Ala Leu Leu Val Arg Tyr Thr Lys Lys Val Pro
```

-continued

```
                 580                 585                 590
Gln Val Ser Thr Pro Thr Leu Val Glu Val Ser Arg Asn Leu Gly Lys
        595                 600                 605

Val Gly Ser Lys Cys Cys Lys His Pro Glu Ala Lys Arg Met Pro Cys
        610                 615                 620

Ala Glu Asp Tyr Leu Ser Val Val Leu Asn Gln Leu Cys Val Leu His
625                 630                 635                 640

Glu Lys Thr Pro Val Ser Asp Arg Val Thr Lys Cys Cys Thr Glu Ser
                645                 650                 655

Leu Val Asn Arg Arg Pro Cys Phe Ser Ala Leu Glu Val Asp Glu Thr
                660                 665                 670

Tyr Val Pro Lys Glu Phe Asn Ala Glu Thr Phe Thr Phe His Ala Asp
                675                 680                 685

Ile Cys Thr Leu Ser Glu Lys Glu Arg Gln Ile Lys Lys Gln Thr Ala
        690                 695                 700

Leu Val Glu Leu Val Lys His Lys Pro Lys Ala Thr Lys Glu Gln Leu
705                 710                 715                 720

Lys Ala Val Met Asp Asp Phe Ala Ala Phe Val Glu Lys Cys Cys Lys
                725                 730                 735

Ala Asp Asp Lys Glu Thr Cys Phe Ala Glu Glu Gly Lys Lys Leu Val
                740                 745                 750

Ala Ala Ser Gln Ala Ala Leu Gly Leu
        755                 760

<210> SEQ ID NO 13
<211> LENGTH: 27
<212> TYPE: DNA
<213> ORGANISM: Artificial Sequence
<220> FEATURE:
<223> OTHER INFORMATION: Primer YA082, synthetic sequence

<400> SEQUENCE: 13
aactatactg aggcaaagga tgtcttc                                    27

<210> SEQ ID NO 14
<211> LENGTH: 27
<212> TYPE: DNA
<213> ORGANISM: Artificial Sequence
<220> FEATURE:
<223> OTHER INFORMATION: Primer YA083, synthetic sequence

<400> SEQUENCE: 14
tgcctcagta tagtttttgc aaacatc                                    27

<210> SEQ ID NO 15
<211> LENGTH: 776
<212> TYPE: PRT
<213> ORGANISM: Artificial Sequence
<220> FEATURE:
<223> OTHER INFORMATION: Amino acid sequence of 22KhGH-HSA

<400> SEQUENCE: 15

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
```

-continued

```
                50                    55                    60

Glu Glu Thr Gln Gln Lys Ser Asn Leu Glu Leu Leu Arg Ile Ser Leu
65                    70                    75                    80

Leu Leu Ile Gln Ser Trp Leu Glu Pro Val Gln Phe Leu Arg Ser Val
                85                    90                    95

Phe Ala Asn Ser Leu Val Tyr Gly Ala Ser Asp Ser Asn Val Tyr Asp
                100                   105                   110

Leu Leu Lys Asp Leu Glu Glu Gly Ile Gln Thr Leu Met Gly Arg Leu
                115                   120                   125

Glu Asp Gly Ser Pro Arg Thr Gly Gln Ile Phe Lys Gln Thr Tyr Ser
    130                   135                   140

Lys Phe Asp Thr Asn Ser His Asn Asp Asp Ala Leu Leu Lys Asn Tyr
145                   150                   155                   160

Gly Leu Leu Tyr Cys Phe Arg Lys Asp Met Asp Lys Val Glu Thr Phe
                165                   170                   175

Leu Arg Ile Val Gln Cys Arg Ser Val Glu Gly Ser Cys Gly Phe Asp
                180                   185                   190

Ala His Lys Ser Glu Val Ala His Arg Phe Lys Asp Leu Gly Glu Glu
                195                   200                   205

Asn Phe Lys Ala Leu Val Leu Ile Ala Phe Ala Gln Tyr Leu Gln Gln
    210                   215                   220

Cys Pro Phe Glu Asp His Val Lys Leu Val Asn Glu Val Thr Glu Phe
225                   230                   235                   240

Ala Lys Thr Cys Val Ala Asp Glu Ser Ala Glu Asn Cys Asp Lys Ser
                245                   250                   255

Leu His Thr Leu Phe Gly Asp Lys Leu Cys Thr Val Ala Thr Leu Arg
                260                   265                   270

Glu Thr Tyr Gly Glu Met Ala Asp Cys Cys Ala Lys Gln Glu Pro Glu
                275                   280                   285

Arg Asn Glu Cys Phe Leu Gln His Lys Asp Asp Asn Pro Asn Leu Pro
    290                   295                   300

Arg Leu Val Arg Pro Glu Val Asp Val Met Cys Thr Ala Phe His Asp
305                   310                   315                   320

Asn Glu Glu Thr Phe Leu Lys Lys Tyr Leu Tyr Glu Ile Ala Arg Arg
                325                   330                   335

His Pro Tyr Phe Tyr Ala Pro Glu Leu Leu Phe Phe Ala Lys Arg Tyr
                340                   345                   350

Lys Ala Ala Phe Thr Glu Cys Cys Gln Ala Ala Asp Lys Ala Ala Cys
                355                   360                   365

Leu Leu Pro Lys Leu Asp Glu Leu Arg Asp Glu Gly Lys Ala Ser Ser
    370                   375                   380

Ala Lys Gln Arg Leu Lys Cys Ala Ser Leu Gln Lys Phe Gly Glu Arg
385                   390                   395                   400

Ala Phe Lys Ala Trp Ala Val Ala Arg Leu Ser Gln Arg Phe Pro Lys
                405                   410                   415

Ala Glu Phe Ala Glu Val Ser Lys Leu Val Thr Asp Leu Thr Lys Val
                420                   425                   430

His Thr Glu Cys Cys His Gly Asp Leu Leu Glu Cys Ala Asp Asp Arg
                435                   440                   445

Ala Asp Leu Ala Lys Tyr Ile Cys Glu Asn Gln Asp Ser Ile Ser Ser
    450                   455                   460

Lys Leu Lys Glu Cys Cys Glu Lys Pro Leu Leu Glu Lys Ser His Cys
465                   470                   475                   480
```

```
Ile Ala Glu Val Glu Asn Asp Glu Met Pro Ala Asp Leu Pro Ser Leu
            485                 490                 495

Ala Ala Asp Phe Val Glu Ser Lys Asp Val Cys Lys Asn Tyr Ala Glu
            500                 505                 510

Ala Lys Asp Val Phe Leu Gly Met Phe Leu Tyr Glu Tyr Ala Arg Arg
            515                 520                 525

His Pro Asp Tyr Ser Val Val Leu Leu Leu Arg Leu Ala Lys Thr Tyr
        530                 535                 540

Glu Thr Thr Leu Glu Lys Cys Cys Ala Ala Ala Asp Pro His Glu Cys
545                 550                 555                 560

Tyr Ala Lys Val Phe Asp Glu Phe Lys Pro Leu Val Glu Glu Pro Gln
            565                 570                 575

Asn Leu Ile Lys Gln Asn Cys Glu Leu Phe Glu Gln Leu Gly Glu Tyr
            580                 585                 590

Lys Phe Gln Asn Ala Leu Leu Val Arg Tyr Thr Lys Lys Val Pro Gln
            595                 600                 605

Val Ser Thr Pro Thr Leu Val Glu Val Ser Arg Asn Leu Gly Lys Val
        610                 615                 620

Gly Ser Lys Cys Cys Lys His Pro Glu Ala Lys Arg Met Pro Cys Ala
625                 630                 635                 640

Glu Asp Tyr Leu Ser Val Val Leu Asn Gln Leu Cys Val Leu His Glu
            645                 650                 655

Lys Thr Pro Val Ser Asp Arg Val Thr Lys Cys Cys Thr Glu Ser Leu
            660                 665                 670

Val Asn Arg Arg Pro Cys Phe Ser Ala Leu Glu Val Asp Glu Thr Tyr
            675                 680                 685

Val Pro Lys Glu Phe Asn Ala Glu Thr Phe Thr Phe His Ala Asp Ile
        690                 695                 700

Cys Thr Leu Ser Glu Lys Glu Arg Gln Ile Lys Lys Gln Thr Ala Leu
705                 710                 715                 720

Val Glu Leu Val Lys His Lys Pro Lys Ala Thr Lys Glu Gln Leu Lys
            725                 730                 735

Ala Val Met Asp Asp Phe Ala Ala Phe Val Glu Lys Cys Cys Lys Ala
            740                 745                 750

Asp Asp Lys Glu Thr Cys Phe Ala Glu Glu Gly Lys Lys Leu Val Ala
            755                 760                 765

Ala Ser Gln Ala Ala Leu Gly Leu
770                 775
```

<210> SEQ ID NO 16
<211> LENGTH: 2427
<212> TYPE: DNA
<213> ORGANISM: Artificial Sequence
<220> FEATURE:
<223> OTHER INFORMATION: Nucleotide sequence containing 22KhGH-HSA gene,
      synthetic sequence

<400> SEQUENCE: 16

```
acgcgtcacc atggctacag gctcccggac gtccctgctc ctggcttttg gcctgctctg      60
cctgccctgg cttcaagagg gcagtgcctt cccaaccatt cccttatcca ggcttttga      120 caacgctatg ctccgcgccc atcgtctgca ccagctggcc tttgacacct accaggagtt      180
tgaagaagcc tatatcccaa aggaacagaa gtattcattc ctgcagaacc cccagacctc      240
cctctgtttc tcagagtcta ttccgacacc ctccaacagg gaggaaacac aacagaaatc      300
```

-continued

```
caacctagag ctgctccgca tctccctgct gctcatccag tcgtggctgg agcccgtgca      360
gttcctcagg agtgtcttcg ccaacagcct ggtgtacggc gcctctgaca gcaacgtcta      420
tgacctccta aaggacctag aggaaggcat ccaaacgctg atggggaggc tggaagatgg      480
cagcccccgg actgggcaga tcttcaagca gacctacagc aagttcgaca caaactcaca      540
caacgatgac gcactactca agaactacgg gctgctctac tgcttcagga aggacatgga      600
caaggtcgag acattcctgc gcatcgtgca gtgccgctct gtggagggca gctgtggctt      660
cgatgcacac aagagtgagg ttgctcatcg gtttaaagat ttgggagaag aaaatttcaa      720
agccttggtg ttgattgcct ttgctcagta tcttcagcag tgtccatttg aagatcatgt      780
aaaattagtg aatgaagtaa ctgaatttgc aaaaacatgt gttgctgatg agtcagctga      840
aaattgtgac aaatcacttc ataccctttt tggagacaaa ttatgcacag ttgcaactct      900
tcgtgaaacc tatggtgaaa tggctgactg ctgtgcaaaa caagaacctg agagaaatga      960
atgcttcttg caacacaaag atgacaaccc aaacctcccc cgattggtga gaccagaggt     1020
tgatgtgatg tgcactgctt ttcatgacaa tgaagagaca ttttttgaaaa aatacttata     1080 tgaaattgcc agaagacatc cttacttta tgccccggaa ctcctttct ttgctaaaag     1140 gtataaagct gcttttacag aatgttgcca agctgctgat aaagctgcct gcctgttgcc     1200
aaagctcgat gaacttcggg atgaagggaa ggcttcgtct gccaaacaga gactcaagtg     1260
tgccagtctc caaaaatttg gagaaagagc tttcaaagca tgggcagtag ctcgcctgag     1320
ccagagattt cccaaagctg agtttgcaga agtttccaag ttagtgacag atcttaccaa     1380
agtccacacg gaatgctgcc atggagatct gcttgaatgt gctgatgaca gggcggacct     1440
tgccaagtat atctgtgaaa atcaagattc gatctccagt aaactgaagg aatgctgtga     1500
aaaacctctg ttggaaaaat cccactgcat tgccgaagtg gaaaatgatg agatgcctgc     1560
tgacttgcct tcattagctg ctgattttgt tgaaagtaag gatgtttgca aaaactatgc     1620
tgaggcaaag gatgtcttcc tgggcatgtt tttgtatgaa tatgcaagaa ggcatcctga     1680
ttactctgtc gtgctgctgc tgagacttgc caagacatat gaaaccactc tagagaagtg     1740
ctgtgccgct gcagatcctc atgaatgcta tgccaaagtg ttcgatgaat ttaaacctct     1800
tgtggaagag cctcagaatt taatcaaaca aaattgtgag ctttttgagc agcttggaga     1860
gtacaaattc cagaatgcgc tattagttcg ttacaccaag aaagtacccc aagtgtcaac     1920
tccaactctt gtagaggtct caagaaacct aggaaaagtg ggcagcaaat gttgtaaaca     1980
tcctgaagca aaaagaatgc cctgtgcaga agactatcta tccgtggtcc tgaaccagtt     2040
atgtgtgttg catgagaaaa cgccagtaag tgacagagtc accaaatgct gcacagaatc     2100
cttggtgaac aggcgaccat gctttttcagc tctggaagtc gatgaaacat acgttcccaa     2160
agagtttaat gctgaaacat tcaccttcca tgcagatata tgcacacttt ctgagaagga     2220
gagacaaatc aagaaacaaa ctgcacttgt tgagctcgtg aaacacaagc ccaaggcaac     2280
aaaagagcaa ctgaaagctg ttatggatga tttcgcagct tttgtagaga agtgctgcaa     2340
ggctgacgat aaggagacct gctttgccga ggagggtaaa aaacttgttg ctgcaagtca     2400
agctgcctta ggcttataag cggccgc                                        2427
```